US010647987B2

(12) United States Patent
Jaschinski et al.

(10) Patent No.: US 10,647,987 B2
(45) Date of Patent: May 12, 2020

(54) APPROACH FOR TREATING INFLAMMATORY DISORDERS

(71) Applicant: Secarna Pharmaceuticals GmbH & Co. KG, Marburg (DE)

(72) Inventors: Frank Jaschinski, Puchheim (DE); Ksenija Schirduan, München (DE); Sven Michel, Bernried (DE)

(73) Assignee: Secama Pharmaceuticals GmbH & Co KG, Marburg (DE)

( * ) Notice: Subject to any disclaimer, the term of this patent is extended or adjusted under 35 U.S.C. 154(b) by 0 days.

(21) Appl. No.: 16/079,588

(22) PCT Filed: Feb. 24, 2017

(86) PCT No.: PCT/EP2017/054374
§ 371 (c)(1),
(2) Date: Aug. 24, 2018

(87) PCT Pub. No.: WO2017/144685
PCT Pub. Date: Aug. 31, 2017

(65) Prior Publication Data
US 2019/0055566 A1    Feb. 21, 2019

(30) Foreign Application Priority Data

Feb. 26, 2016  (EP) .................................. 16000468
Oct. 27, 2016  (EP) .................................. 16002305

(51) Int. Cl.
*A61K 48/00*    (2006.01)
*C12N 15/11*    (2006.01)
(Continued)

(52) U.S. Cl.
CPC .......... *C12N 15/1138* (2013.01); *A61P 25/28* (2018.01); *A61P 29/00* (2018.01);
(Continued)

(58) Field of Classification Search
CPC ............ C12N 15/1138; C12N 2310/11; C12N 2310/127; C12N 2310/315;
(Continued)

(56) References Cited

U.S. PATENT DOCUMENTS 7,897,583 B2 *  3/2011  McKay .............. C12N 15/1137
514/44 A

FOREIGN PATENT DOCUMENTS

CN            102732562 A   10/2012
WO    WO 2004/024879 A2    3/2004
(Continued)

OTHER PUBLICATIONS

Kenney et al. (Blood, 1998 vol. 92:1721-1727).*
(Continued)

*Primary Examiner* — Terra C Gibbs
(74) *Attorney, Agent, or Firm* — BakerHostetler

(57) ABSTRACT

The present invention relates to a novel approach for treating inflammatory disorders and other diseases, which is based on targeting ROR gamma t mRNA. The invention is directed to oligonucleotides comprising 10 to 22 modified or unmodified nucleotides complementary to specifically selected regions of the RORC, transcript variant 2 mRNA (RORC2), which codes for the ROR gamma t protein.

12 Claims, 13 Drawing Sheets
(3 of 13 Drawing Sheet(s) Filed in Color)

Specification includes a Sequence Listing.

(51) Int. Cl.
*C07H 21/02* (2006.01)
*C07H 21/04* (2006.01)
*C12N 15/113* (2010.01)
*A61P 25/28* (2006.01)
*A61P 29/00* (2006.01)
*A61P 35/00* (2006.01)

(52) U.S. Cl.
CPC ............ *A61P 35/00* (2018.01); *C12N 2310/11* (2013.01); *C12N 2310/127* (2013.01); *C12N 2310/315* (2013.01); *C12N 2310/321* (2013.01); *C12N 2310/3231* (2013.01); *C12N 2310/341* (2013.01); *C12N 2310/346* (2013.01)

(58) Field of Classification Search
CPC ...... C12N 2310/321; C12N 2310/3231; C12N 2310/341; C12N 2310/346; A61P 25/28
See application file for complete search history.

(56) References Cited

FOREIGN PATENT DOCUMENTS

| WO | WO 2005/033314 A2 | 4/2005 |
| WO | WO 2006/007486 A2 | 1/2006 |
| WO | WO 2008/113832 A2 | 9/2008 |
| WO | WO 2011/113015 A2 | 9/2011 |
| WO | WO 2012/129394 A1 | 9/2012 |
| WO | WO 2014/154843 A1 | 10/2014 |

OTHER PUBLICATIONS

Burgler et al. "RORC2 is Involved in T Cell Polarization through Interaction with the FOXP3 Promoter", J Immunol, 2010, 184, 6161-6169.

Hakemi et al., "RORC2 Gene Silencing in Human Th17 Cells by siRNA: Design and Evaluation of Highly Efficient siRNA", Avicenna J Med Biotech, 2013, 5(1), 10-19.

Jepsen et al., "LNA-Antisense rivals siRNA for gene silencing", Current Opinion in Drug Discovery & Development, 2004, 7(2), 188-194.

Lin et al., "Targeting Th17 Cells with Small Molecules and Small Interference RNA", Hindawi Publishing Corporation, Mediators of Inflammation, 2015, vol. 2015 Article 290657, 11 pages.

Song et al., "CD4 aptamer-RORγt shRNA Chimera Inhibits IL-17 Syntehesis by Human CD4+ T cells", Biochem Biophys Res Commun, 2014, 452(4), 1040-1045.

Stanton et al., "Chemical Modification Study of Antisense Gapmers", Nucleic Acid Therapeutics, 2012, 22(5), 344-359.

Webering, "On the role of the α-melanocyte-stimulating hormone (α-MSH) and retinoid-related-orphan receptor γt (RORΔt) in immunopathogenesis of bronchial asthma", Ph.D. Thesis, University of Lubeck, 2015, 60 pages, English translation.

* cited by examiner

Figure 1 (SEQ ID No 1):

```
   1  AGAGAGCTAG GTGCAGAGCT TCAGGCTGAG GCGCTGCTGA GAGGGCCTCG CCCCGCCTCT
  61  GCCGCCAGCT GCACCCCACT CCTGGACCAC CCCTGCTGA GAAGGACAGG GAGCCAAGGC
 121  CGGCAGAGCC AAGGCTCAGT CATGAGAACa caaattgaag tgatcccttg caaaatctgt
 181  gggacaagt cgtctggat ccactacggg gttatcacct gtgaggggtg caagggcttc
 241  ttccgccgga gccagcgctg taacgcggcc tactcctgca cccgtcagca gaactgcccc
 301  atcgaccgca ccagccgaaa ccgatgccag cactgccgcc tgcagaaatg cctggcgctg
 361  ggcatgtccc gagatgctgt caagttcggc cgcatgtcgg agaagcagag ggacagcctg
 421  catgcagaag tgcagaaaca gctgcagcag cggcaacagc agaacagga accagtggtc
 481  aagaccctc cagcagggc ccaaggagca gataccctca cctacaccct gggctcccca
 541  gacgggcagc tgccccctggg ctcctcgcct gacctgcctg aggcttctgc ctgtccccct
 601  ggcctcctga aagcctcagg cttctgggcc tcatattcca acaacttggc caaggcaggg
 661  ctcaatgggg cctcatgcca ccttgaatac agccctgagc gggcaaggc tgaggcaga
 721  gagagcttct atagcacagg gatgtggact acccctgacc gatgtggact tcgttttgag
 781  gaacacaggc atcctgggct tggggaactg ggacagggcc gccacctat cggcagccc
 841  agtttccgca gcacacggga ggcaccctat gccctcccta cagagataga cagaagggga
 901  cagagcgtct gcaagtccta caggagaca ggctgcagctgc ggctgggaga cctgctgcgg
 961  cagcgctcca acatcttctc ccggggagaa gtgactggct accagaggaa gtccatgtgg
1021  gagatgtggg aacggtgtgc ccaccactc accgaggcca ttcagtacgt ggtggagttc
1081  gccagaggc tctcaggct tatggagctc tgccagaatg accagattgt gcttctcaaa
1141  gcaggagcaa tggaagtgt gctggttagg gctggtgccc ggg ctacagc tgacaacgc
1201  acggtctttt ttgaaggcaa atacgtggc atggagctgt tccgacctt gggtgcagcc
1261  gagctcatca gctccatcct tgacttctcc cactcctcc gtgccttgca cttttccgag
1321  gatgagattg ccctctacac agcccttgtt ctcatcaatg ctcatcggcc ccatcggcc aggctccaa
```

Figure 1 (continued):

```
1381 gagaaaagga aagtagaaca gctgcagtac aatctggagc tggcctttca tcatcatctc
1441 tgcaagactc atcgccaaag catcctggca agctgccac ccaagggaa gcttcggagc
1501 ctgtgtagcc agcatgtgga aaggctgcag atcttccagc acctccaccc catcgtggtc
1561 caagccgctt tccctccact ctacaaggag ctcttcagca ctgaaaccga gtcacctgtg
1621 gggctgtcca agtgacctgg aagagggact cctgcctct ccctatggcc tgctgccca
1681 cctccctgga cccgttcca ccctcaccct tttccttcc catgaaccct ggaggtggt
1741 cccaccagc tctttgaaag tgagcagatg ctggcgctgg ctttctgtca gcaggccggc
1801 ctggcagtgg gacaatcgcc agagggtggg gctgcagaa caccatctcc agcctcagct
1861 ttgacctgtc tcattccca tattccttca cacccagctt ctggaaggca tggggtggct
1921 gggatttaag gacttctggg ggaccaagac atccctcaaga aaacaggggc atccagggct
1981 ccctgatga atagaatgca attcattcag aagctcagaa gctaagaata agcctttgaa
2041 atacctcatt gcatttccct ttggcttcg gcttgggag atggatcaag ctagagact
2101 ggcagtgaga gcccagaagg acctgtataa aatgaatctg gagcttttaca tttctgcct
2161 ctgccttcct cccagctcag caaggaagta tttgggcacc ctaccctta cctggggtct
2221 aaccaaaaat ggatgggatg aggatgagag gctggagata attgttttat gggatttggg
2281 tgtgggacta gggtacaatg aaggccaaga gcatctcaga catagagtta aaactcaaac
2341 ctcttatgtg cactttaaag atagactta caaatctgat caaatcggca cagagacaca
2401 tatccataca caggtgaaac acatacagac cttatccttg ggggctggca tcatgcagtt ccagagacct
2461 atgaacctga cacaatctct cttatccttg agggaggagc ttggaggagc ctagaggcct
2521 caggggaaag tcccaatcct gagggaccct cccaaacatt tccatggtgc tccagtccac
2581 tgatcttggg tctgggtga tccaaatacc acccagctc cagctgtctt ctaccactag
2641 aagacccaag agaagcagaa gtcgctcgca gtccagctc caggtcagtc ggaaggcaag atcagatcct
2701 ggaggacttt cctggcctgc ccgcccagcc tgctcttgtt gtggagaagg aagcagatgt
2761 gatcacatca cccgtcatt gggcaccgct gactccagca tggaggacac caggagcag
2821 ggcctgggcc tgtttcccca gctgtgatct tgcccagaac ctctcttggc ttcataaaca
```

Figure 1 (continued):

```
2881 gctgtgaacc ctcccctgag ggattaacag caatgatggg cagtcgtgga gttgggggg
2941 ttggggtgg gattgtgtcc tctaagggga cgggttcatc tgagtaaaca taaacccaa
3001 cttgtgccat tctttataaa atgattttaa aggcaaaaaa aaaaaaaaaa aaaa
```

2',4'-BNA
(2001)

3'-amino-2',4'-BNA
(2001)

2',4'-BNA-2-pyridone
(2001)

2',4'-BNA
(2001)

2',4'-ENA
(2001)

2',4'-BNA-1-isoquinolone
(2003)

2',4'-BNA/LNA

Constrained Ethyl Bridged Nucleic Acid (c-ET)

ates, was created on Aug. 19, 2019, and is 37 KB. The entire content is incorporated herein by reference in its entirety.

SEQUENCE LISTING

<160> NUMBER OF SEQ ID NOS: 80

<210> SEQ ID NO 1
<211> LENGTH: 3054
<212> TYPE: DNA
<213> ORGANISM: Homo sapiens

<400> SEQUENCE: 1

```
agagagctag gtgcagagct tcaggctgag gcgctgctga gagggcctcg ccccgcctct       60
gccgccagct gcaccccact cctggaccac cccctgctga aaggacagg gagccaaggc      120
cggcagagcc aaggctcagt catgagaaca caaattgaag tgatcccttg caaaatctgt      180
ggggacaagt cgtctgggat ccactacggg gttatcacct gtgaggggtg caagggcttc     240
ttccgccgga gccagcgctg taacgcggcc tactcctgca cccgtcagca gaactgcccc     300
atcgaccgca ccagccgaaa ccgatgccag cactgccgcc tgcagaaatg cctggcgctg     360
ggcatgtccc gagatgctgt caagttcggc cgcatgtcca agaagcagag ggacagcctg     420
catgcagaag tgcagaaaca gctgcagcag cggcaacagc agcaacagga accagtggtc     480
aagaccctc cagcagggc ccaaggagca gatacctca cctacacctt ggggctccca       540
gacgggcagc tgcccctggg ctcctcgcct gacctgctg aggcttctgc ctgtcccct        600
ggcctcctga aagcctcagg ctctgggccc tcatattcca caacttggc caaggcaggg       660
ctcaatgggg cctcatgcca ccttgaatac agccctgagc ggggcaaggc tgagggcaga      720
gagagcttct atagcacagg cagccagctg accctgacc gatgtggact tcgtttttgag      780
gaacacaggc atcctgggct tggggaactg ggacagggcc cagacagcta cggcagcccc      840
agttttccgca gcacaccgga ggcacccctat gcctccctga cagagataga gcacctggtg      900
cagagcgtct gcaagtccta cagggagaca tgccagctgc ggctggagga cctgctgcgg      960
cagcgctcca acatcttctc ccgggaggaa gtgactggct accagaggaa gtccatgtgg     1020
gagatgtggg aacggtgtgc ccaccacctc accgaggcca ttcagtacgt ggtggagttc     1080
gccaagaggc tctcaggctt tatggagctc tgccagaatg accagattgt gcttctcaaa     1140
gcaggagcaa tggaagtggt gctggttagg atgtgccggg cctacaatgc tgacaaccgc     1200
acggtctttt ttgaaggcaa atacggtggc atggagctgt tccgagcctt gggctgcagc     1260
gagctcatca gctccatctt tgacttctcc cactccctaa gtgccttgca cttttccgag     1320
gatgagattg ccctctacac agcccttgtt ctcatcaatg cccatcggcc agggctccaa     1380
gagaaaagga aagtagaaca gctgcagtac aatctggagc tggccttttca tcatcatctc     1440
tgcaagactc atcgccaaag catcctggca aagctgccac ccaaggggaa gcttcggagc     1500
```

| | |
|---|---|
| ctgtgtagcc agcatgtgga aaggctgcag atcttccagc acctccaccc catcgtggtc | 1560 |
| caagccgctt tccctccact ctacaaggag ctcttcagca ctgaaaccga gtcacctgtg | 1620 |
| gggctgtcca agtgacctgg aagagggact ccttgcctct ccctatggcc tgctggccca | 1680 |
| cctccctgga ccccgttcca ccctcaccct tttccttcc catgaaccct ggagggtggt | 1740 |
| ccccaccagc tctttggaag tgagcagatg ctgcggctgg ctttctgtca gcaggccggc | 1800 |
| ctggcagtgg gacaatcgcc agagggtggg gctggcagaa caccatctcc agcctcagct | 1860 |
| ttgacctgtc tcatttccca tattccttca cacccagctt ctggaaggca tggggtggct | 1920 |
| gggatttaag gacttctggg ggaccaagac atcctcaaga aaacaggggc atccagggct | 1980 |
| ccctggatga atagaatgca attcattcag aagctcagaa gctaagaata agcctttgaa | 2040 |
| atacctcatt gcatttccct ttgggcttcg gcttggggag atggatcaag ctcagagact | 2100 |
| ggcagtgaga gcccagaagg acctgtataa aatgaatctg gagctttaca ttttctgcct | 2160 |
| ctgccttcct cccagctcag caaggaagta tttgggcacc ctacccttta cctgggggtct | 2220 |
| aaccaaaaat ggatgggatg aggatgagag gctggagata attgttttat gggatttggg | 2280 |
| tgtgggacta gggtacaatg aaggccaaga gcatctcaga catagagtta aaactcaaac | 2340 |
| ctcttatgtg cactttaaag atagacttta ggggctggca caaatctgat cagagacaca | 2400 |
| tatccataca caggtgaaac acatacagac tcaacagcaa tcatgcagtt ccagagacac | 2460 |
| atgaacctga cacaatctct cttatccttg aggccacagc ttggaggagc ctagaggcct | 2520 |
| caggggaaag tcccaatcct gagggaccct cccaaacatt tccatggtgc tccagtccac | 2580 |
| tgatcttggg tctggggtga tccaaatacc accccagctc cagctgtctt ctaccactag | 2640 |
| aagacccaag agaagcagaa gtcgctcgca ctggtcagtc ggaaggcaag atcagatcct | 2700 |
| ggaggacttt cctggcctgc ccgccagccc tgctcttgtt gtggagaagg aagcagatgt | 2760 |
| gatcacatca ccccgtcatt gggcaccgct gactccagca tggaggacac cagggagcag | 2820 |
| ggcctgggcc tgtttcccca gctgtgatct tgcccagaac ctctcttggc ttcataaaca | 2880 |
| gctgtgaacc ctcccctgag ggattaacag caatgatggg cagtcgtgga gttggggggg | 2940 |
| ttgggggtgg gattgtgtcc tctaagggga cgggttcatc tgagtaaaca taaaccccaa | 3000 |
| cttgtgccat tctttataaa atgatttaa aggcaaaaaa aaaaaaaaaa aaaa | 3054 |

```
<210> SEQ ID NO 2
<211> LENGTH: 15
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(16)
<223> OTHER INFORMATION: Phosphorothioate linkages
<220> FEATURE:
<221> NAME/KEY: misc_feature
<222> LOCATION: (1)..(16)
<223> OTHER INFORMATION: LNA-modifications at positions 1, 2, 3, 13, 14,
      15

<400> SEQUENCE: 2
ttcaatttgt gttct                                                    15

<210> SEQ ID NO 3
<211> LENGTH: 17
<212> TYPE: DNA
<213> ORGANISM: Artificial Sequence
```

-continued

```
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(17)
<223> OTHER INFORMATION: LNA-modifications at positions 1, 2, 3, 15, 16,
      17
<220> FEATURE:
<221> NAME/KEY: misc_feature
<222> LOCATION: (1)..(17)
<223> OTHER INFORMATION: Phosphorothioate linkages

<400> SEQUENCE: 3
tttgtgttct catgact                                                          17

<210> SEQ ID NO 4
<211> LENGTH: 16
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(16)
<223> OTHER INFORMATION: LNA-modifications at positions 1, 2, 3, 14, 15,
      16
<220> FEATURE:
<221> NAME/KEY: misc_feature
<222> LOCATION: (1)..(16)
<223> OTHER INFORMATION: Phosphorothioate linkages

<400> SEQUENCE: 4
tttgtgttct catgac                                                           16

<210> SEQ ID NO 5
<211> LENGTH: 16
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(16)
<223> OTHER INFORMATION: LNA-modifications at positions 1, 2, 3, 15, 16
<220> FEATURE:
<221> NAME/KEY: misc_feature
<222> LOCATION: (1)..(16)
<223> OTHER INFORMATION: Phosphorothioate linkages

<400> SEQUENCE: 5
ttcaatttgt gttctc                                                           16

<210> SEQ ID NO 6
<211> LENGTH: 17
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(17)
<223> OTHER INFORMATION: LNA-modifications at positions 1, 2, 4, 15, 16,
      17
<220> FEATURE:
<221> NAME/KEY: misc_feature
<222> LOCATION: (1)..(17)
<223> OTHER INFORMATION: Phosphorothioate linkages

<400> SEQUENCE: 6
```
acttcaattt gtgttct                                                    17

<210> SEQ ID NO 7
<211> LENGTH: 17
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(17)
<223> OTHER INFORMATION: LNA-modifications at positions 1, 2, 3, 15, 16,
      17
<220> FEATURE:
<221> NAME/KEY: misc_feature
<222> LOCATION: (1)..(17)
<223> OTHER INFORMATION: Phosphorothioate linkages

<400> SEQUENCE: 7
cacttcaatt tgtgttc                                                    17

<210> SEQ ID NO 8
<211> LENGTH: 16
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(16)
<223> OTHER INFORMATION: LNA-modifications at positions 1, 2, 4, 14, 15,
      16
<220> FEATURE:
<221> NAME/KEY: misc_feature
<222> LOCATION: (1)..(16)
<223> OTHER INFORMATION: Phosphorothioate linkages

<400> SEQUENCE: 8
tcaatttgtg ttctca                                                     16

<210> SEQ ID NO 9
<211> LENGTH: 15
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(15)
<223> OTHER INFORMATION: LNA-modifications at positions 1, 2, 13, 15
<220> FEATURE:
<221> NAME/KEY: misc_feature
<222> LOCATION: (1)..(15)
<223> OTHER INFORMATION: Phosphorothioate linkages

<400> SEQUENCE: 9
gtgttctcat gactg                                                      15

<210> SEQ ID NO 10
<211> LENGTH: 17
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(17)

```
<223> OTHER INFORMATION: LNA-modifications at positions 1, 2, 3, 15, 16,
      17
<220> FEATURE:
<221> NAME/KEY: misc_feature
<222> LOCATION: (1)..(17)
<223> OTHER INFORMATION: Phosphorothioate linkages

<400> SEQUENCE: 10
atttgtgttc tcatgac                                                      17

<210> SEQ ID NO 11
<211> LENGTH: 17
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(17)
<223> OTHER INFORMATION: LNA-modifications at positions 1, 2, 14, 15, 17
<220> FEATURE:
<221> NAME/KEY: misc_feature
<222> LOCATION: (1)..(17)
<223> OTHER INFORMATION: Phosphorothioate linkages

<400> SEQUENCE: 11
tcaatttgtg ttctcat                                                      17

<210> SEQ ID NO 12
<211> LENGTH: 16
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(16)
<223> OTHER INFORMATION: LNA-modifications at positions 1, 2, 3, 15, 16
<220> FEATURE:
<221> NAME/KEY: misc_feature
<222> LOCATION: (1)..(16)
<223> OTHER INFORMATION: Phosphorothioate linkages

<400> SEQUENCE: 12
atttgtgttc tcatga                                                       16

<210> SEQ ID NO 13
<211> LENGTH: 17
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(17)
<223> OTHER INFORMATION: LNA-modifications at positions 1, 3, 4, 16, 17
<220> FEATURE:
<221> NAME/KEY: misc_feature
<222> LOCATION: (1)..(17)
<223> OTHER INFORMATION: Phosphorothioate linkages

<400> SEQUENCE: 13
gtgttctcat gactgag                                                      17

<210> SEQ ID NO 14
<211> LENGTH: 16
<212> TYPE: DNA
<213> ORGANISM: Artificial Sequence
```

```
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(16)
<223> OTHER INFORMATION: LNA-modifications at positions 1, 2, 3, 14, 15,
      16
<220> FEATURE:
<221> NAME/KEY: misc_feature
<222> LOCATION: (1)..(16)
<223> OTHER INFORMATION: Phosphorothioate linkages

<400> SEQUENCE: 14
gtgttctcat gactga                                                          16

<210> SEQ ID NO 15
<211> LENGTH: 16
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(16)
<223> OTHER INFORMATION: LNA-modifications at positions 1, 2, 4, 14, 15,
      16
<220> FEATURE:
<221> NAME/KEY: misc_feature
<222> LOCATION: (1)..(16)
<223> OTHER INFORMATION: Phosphorothioate linkages

<400> SEQUENCE: 15
ttgtgttctc atgact                                                          16

<210> SEQ ID NO 16
<211> LENGTH: 17
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(17)
<223> OTHER INFORMATION: LNA-modifications at positions 1, 4, 5, 15, 16,
      17
<220> FEATURE:
<221> NAME/KEY: misc_feature
<222> LOCATION: (1)..(17)
<223> OTHER INFORMATION: Phosphorothioate linkages

<400> SEQUENCE: 16
tgtgttctca tgactga                                                         17

<210> SEQ ID NO 17
<211> LENGTH: 16
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(16)
<223> OTHER INFORMATION: LNA-modifications at positions 1, 3, 14, 16
<220> FEATURE:
<221> NAME/KEY: misc_feature
<222> LOCATION: (1)..(16)
<223> OTHER INFORMATION: Phosphorothioate linkages

<400> SEQUENCE: 17
```
gtgttctcat gactga                                               16

<210> SEQ ID NO 18
<211> LENGTH: 16
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(16)
<223> OTHER INFORMATION: LNA-modifications at positions 1, 2, 14, 16
<220> FEATURE:
<221> NAME/KEY: misc_feature
<222> LOCATION: (1)..(16)
<223> OTHER INFORMATION: Phosphorothioate linkages

<400> SEQUENCE: 18
cttggctccc tgtcct                                               16

<210> SEQ ID NO 19
<211> LENGTH: 16
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(16)
<223> OTHER INFORMATION: LNA-modifications at positions 1, 2, 4, 14, 15,
      16
<220> FEATURE:
<221> NAME/KEY: misc_feature
<222> LOCATION: (1)..(16)
<223> OTHER INFORMATION: Phosphorothioate linkages

<400> SEQUENCE: 19
acttcaattt gtgttc                                               16

<210> SEQ ID NO 20
<211> LENGTH: 17
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(17)
<223> OTHER INFORMATION: LNA-modifications at positions 1, 2, 5, 15, 16,
      17
<220> FEATURE:
<221> NAME/KEY: misc_feature
<222> LOCATION: (1)..(17)
<223> OTHER INFORMATION: Phosphorothioate linkages

<400> SEQUENCE: 20
tcacttcaat ttgtgtt                                              17

<210> SEQ ID NO 21
<211> LENGTH: 17
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(17)

```
<223> OTHER INFORMATION: LNA-modifications at positions 1, 3, 4, 13, 15,
      17
<220> FEATURE:
<221> NAME/KEY: misc_feature
<222> LOCATION: (1)..(17)
<223> OTHER INFORMATION: Phosphorothioate linkages

<400> SEQUENCE: 21
caatttgtgt tctcatg                                                  17

<210> SEQ ID NO 22
<211> LENGTH: 16
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(16)
<223> OTHER INFORMATION: LNA-modifications at positions 1, 3, 14, 15, 16
<220> FEATURE:
<221> NAME/KEY: misc_feature
<222> LOCATION: (1)..(16)
<223> OTHER INFORMATION: Phosphorothioate linkages

<400> SEQUENCE: 22
gcagctggcg gcagag                                                   16

<210> SEQ ID NO 23
<211> LENGTH: 17
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(17)
<223> OTHER INFORMATION: Phosphorothioate linkages
<220> FEATURE:
<221> NAME/KEY: misc_feature
<222> LOCATION: (1)..(17)
<223> OTHER INFORMATION: LNA-modifications at positions 1, 2, 3, 15, 16,
      and 17

<400> SEQUENCE: 23
ttcaatttgt gttctca                                                  17

<210> SEQ ID NO 24
<211> LENGTH: 17
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(17)
<223> OTHER INFORMATION: Phosphorothioate linkages
<220> FEATURE:
<221> NAME/KEY: misc_feature
<222> LOCATION: (1)..(17)
<223> OTHER INFORMATION: LNA-modifications at positions 1, 2, 3, 15, 16,
      and 17

<400> SEQUENCE: 24
gtgttctcat gactgag                                                  17

<210> SEQ ID NO 25
<211> LENGTH: 16
```

```
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(16)
<223> OTHER INFORMATION: Phosphorothioate linkages
<220> FEATURE:
<221> NAME/KEY: misc_feature
<222> LOCATION: (1)..(16)
<223> OTHER INFORMATION: LNA-modifications at positions 1, 2, 14 and 15

<400> SEQUENCE: 25
gtgttctcat gactga                                             16

<210> SEQ ID NO 26
<211> LENGTH: 16
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(16)
<223> OTHER INFORMATION: Phosphorothioate linkages
<220> FEATURE:
<221> NAME/KEY: misc_feature
<222> LOCATION: (1)..(16)
<223> OTHER INFORMATION: LNA-modifications at positions 1, 2, 14 and 15

<400> SEQUENCE: 26
tcaatttgtg ttctca                                             16

<210> SEQ ID NO 27
<211> LENGTH: 16
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(16)
<223> OTHER INFORMATION: Phosphorothioate linkages
<220> FEATURE:
<221> NAME/KEY: misc_feature
<222> LOCATION: (1)..(16)
<223> OTHER INFORMATION: LNA-modifications at positions 1, 2, 3, 14 and
      15

<400> SEQUENCE: 27
gtgttctcat gactga                                             16

<210> SEQ ID NO 28
<211> LENGTH: 16
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(16)
<223> OTHER INFORMATION: Phosphorothioate linkages
<220> FEATURE:
<221> NAME/KEY: misc_feature
<222> LOCATION: (1)..(16)
<223> OTHER INFORMATION: LNA-modifications at positions 1, 2, 3, 15, and
      16
```

-continued

<400> SEQUENCE: 28
gtgttctcat gactga                                                  16

<210> SEQ ID NO 29
<211> LENGTH: 17
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(17)
<223> OTHER INFORMATION: Phosphorothioate linkages
<220> FEATURE:
<221> NAME/KEY: misc_feature
<222> LOCATION: (1)..(17)
<223> OTHER INFORMATION: LNA-modifications at positions 1, 3, 15, 16,
      and 17

<400> SEQUENCE: 29
gtgttctcat gactgag                                                 17

<210> SEQ ID NO 30
<211> LENGTH: 17
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(17)
<223> OTHER INFORMATION: Phosphorothioate linkages
<220> FEATURE:
<221> NAME/KEY: misc_feature
<222> LOCATION: (1)..(17)
<223> OTHER INFORMATION: LNA-modifications at positions 1, 2, 3, 15, 16,
      and 17

<400> SEQUENCE: 30
acttcaattt gtgttct                                                 17

<210> SEQ ID NO 31
<211> LENGTH: 17
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(17)
<223> OTHER INFORMATION: Phosphorothioate linkages
<220> FEATURE:
<221> NAME/KEY: misc_feature
<222> LOCATION: (1)..(17)
<223> OTHER INFORMATION: LNA-modifications at positions 1, 2, 3, 15, and
      17

<400> SEQUENCE: 31
gaagctctgc acctagc                                                 17

<210> SEQ ID NO 32
<211> LENGTH: 16
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:

```
<221> NAME/KEY: misc_feature
<222> LOCATION: (1)..(16)
<223> OTHER INFORMATION: Phosphorothioate linkages
<220> FEATURE:
<221> NAME/KEY: misc_feature
<222> LOCATION: (1)..(16)
<223> OTHER INFORMATION: LNA-modifications at positions 1, 3, 15, and 16

<400> SEQUENCE: 32
gctctgcacc tagctc                                                        16

<210> SEQ ID NO 33
<211> LENGTH: 15
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(15)
<223> OTHER INFORMATION: Phosphorothioate linkages
<220> FEATURE:
<221> NAME/KEY: misc_feature
<222> LOCATION: (1)..(15)
<223> OTHER INFORMATION: LNA-modifications at positions 1, 3, 13, 14,
      and 15

<400> SEQUENCE: 33
cgaggccctc tcagc                                                         15

<210> SEQ ID NO 34
<211> LENGTH: 16
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(16)
<223> OTHER INFORMATION: Phosphorothioate linkages
<220> FEATURE:
<221> NAME/KEY: misc_feature
<222> LOCATION: (1)..(16)
<223> OTHER INFORMATION: LNA-modifications at positions 1, 2, 15, and 16

<400> SEQUENCE: 34
cttggctccc tgtcct                                                        16

<210> SEQ ID NO 35
<211> LENGTH: 15
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(15)
<223> OTHER INFORMATION: Phosphorothioate linkages
<220> FEATURE:
<221> NAME/KEY: misc_feature
<222> LOCATION: (1)..(15)
<223> OTHER INFORMATION: LNA-modifications at positions 1, 3, 13, 14,
      and 15

<400> SEQUENCE: 35
ggcgaggccc tctca                                                         15

<210> SEQ ID NO 36
```

```
<211> LENGTH: 14
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(14)
<223> OTHER INFORMATION: LNA-modifications at positions 1, 2, 3, 12, and
      14

<400> SEQUENCE: 36
aagctctgca ccta                                                        14

<210> SEQ ID NO 37
<211> LENGTH: 15
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(15)
<223> OTHER INFORMATION: Phosphorothioate linkages
<220> FEATURE:
<221> NAME/KEY: misc_feature
<222> LOCATION: (1)..(15)
<223> OTHER INFORMATION: LNA-modifications at positions 1, 2, 3, 13, 14,
      and 15

<400> SEQUENCE: 37
tgtgttctca tgact                                                       15

<210> SEQ ID NO 38
<211> LENGTH: 16
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(16)
<223> OTHER INFORMATION: Phosphorothioate linkages
<220> FEATURE:
<221> NAME/KEY: misc_feature
<222> LOCATION: (1)..(16)
<223> OTHER INFORMATION: LNA-modifications at positions 1, 2, 3, 14, 15,
      and 16

<400> SEQUENCE: 38
gaagctctgc acctag                                                      16

<210> SEQ ID NO 39
<211> LENGTH: 15
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(15)
<223> OTHER INFORMATION: Phosphorothioate linkages
<220> FEATURE:
<221> NAME/KEY: misc_feature
<222> LOCATION: (1)..(15)
```

<223> OTHER INFORMATION: LNA-modifications at positions 1, 2, 3, 13, and
      15

<400> SEQUENCE: 39
ttggctccct gtcct                                                          15

<210> SEQ ID NO 40
<211> LENGTH: 33
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(33)
<223> OTHER INFORMATION: LNA-modifications at positions 1, 2, 3, 31, 32,
      33

<400> SEQUENCE: 40
tcacttcaag gctagctaca acgattgtgt tct                                      33

<210> SEQ ID NO 41
<211> LENGTH: 33
<212> TYPE: DNA
<213> ORGANISM: Artificial Sequence
<220> FEATURE:
<223> OTHER INFORMATION: Artificial DNAzyme with LNA modifications
<220> FEATURE:
<221> NAME/KEY: misc_feature
<222> LOCATION: (1)..(33)
<223> OTHER INFORMATION: LNA-modifications at positions 1, 7, 27, 33

<400> SEQUENCE: 41
tcacttcaag gctagctaca acgattgtgt tct                                      33

<210> SEQ ID NO 42
<211> LENGTH: 35
<212> TYPE: DNA
<213> ORGANISM: Artificial Sequence
<220> FEATURE:
<223> OTHER INFORMATION: Artificial DNAzyme with LNA modifications
<220> FEATURE:
<221> NAME/KEY: misc_feature
<222> LOCATION: (1)..(35)
<223> OTHER INFORMATION: LNA-modifications at positions 1, 4, 24, 25,
      34, 35

<400> SEQUENCE: 42
cttcaaggct agctacaacg attgtgttct catga                                    35

<210> SEQ ID NO 43
<211> LENGTH: 33
<212> TYPE: DNA
<213> ORGANISM: Artificial Sequence
<220> FEATURE:
<223> OTHER INFORMATION: Artificial DNAzyme with LNA modifications
<220> FEATURE:
<221> NAME/KEY: misc_feature
<222> LOCATION: (1)..(33)
<223> OTHER INFORMATION: LNA-modifications at positions 1, 4, 24, 33

<400> SEQUENCE: 43
cttcaaggct agctacaacg attgtgttct cat                                      33

<210> SEQ ID NO 44
<211> LENGTH: 30
<212> TYPE: DNA
<213> ORGANISM: Artificial Sequence

```
<220> FEATURE:
<223> OTHER INFORMATION: Artificial DNAzyme with LNA modifications
<220> FEATURE:
<221> NAME/KEY: misc_feature
<222> LOCATION: (1)..(30)
<223> OTHER INFORMATION: LNA-modifications at positions 1, 5, 27, 30

<400> SEQUENCE: 44
acttcaaggc tagctacaac gattgtgttc                                        30

<210> SEQ ID NO 45
<211> LENGTH: 31
<212> TYPE: DNA
<213> ORGANISM: Artificial Sequence
<220> FEATURE:
<223> OTHER INFORMATION: Artificial DNAzyme with LNA modifications
<220> FEATURE:
<221> NAME/KEY: misc_feature
<222> LOCATION: (1)..(31)
<223> OTHER INFORMATION: LNA-modifications at positions 1, 28, 31

<400> SEQUENCE: 45
ttgtgttctc aggctagcta caacgagact g                                      31

<210> SEQ ID NO 46
<211> LENGTH: 33
<212> TYPE: DNA
<213> ORGANISM: Artificial Sequence
<220> FEATURE:
<223> OTHER INFORMATION: Artificial DNAzyme with LNA modifications
<220> FEATURE:
<221> NAME/KEY: misc_feature
<222> LOCATION: (1)..(33)
<223> OTHER INFORMATION: LNA-modifications at positions 1, 2, 29, 33

<400> SEQUENCE: 46
ttctcatgag gctagctaca acgatgagcc ttg                                    33

<210> SEQ ID NO 47
<211> LENGTH: 29
<212> TYPE: DNA
<213> ORGANISM: Artificial Sequence
<220> FEATURE:
<223> OTHER INFORMATION: Artificial DNAzyme with LNA modifications
<220> FEATURE:
<221> NAME/KEY: misc_feature
<222> LOCATION: (1)..(29)
<223> OTHER INFORMATION: LNA-modifications at positions 1, 3, 26, 29

<400> SEQUENCE: 47
tcatgaggct agctacaacg atgagcctt                                         29

<210> SEQ ID NO 48
<211> LENGTH: 33
<212> TYPE: DNA
<213> ORGANISM: Artificial Sequence
<220> FEATURE:
<223> OTHER INFORMATION: Artificial DNAzyme with LNA modifications
<220> FEATURE:
<221> NAME/KEY: misc_feature
<222> LOCATION: (1)..(33)
<223> OTHER INFORMATION: LNA-modifications at positions 1, 5, 32, 33

<400> SEQUENCE: 48
agctctgcag gctagctaca acgactagct ctc                                    33

<210> SEQ ID NO 49
<211> LENGTH: 32
<212> TYPE: DNA
```

<213> ORGANISM: Artificial Sequence
<220> FEATURE:
<223> OTHER INFORMATION: Artificial DNAzyme with LNA modifications
<220> FEATURE:
<221> NAME/KEY: misc_feature
<222> LOCATION: (1)..(32)
<223> OTHER INFORMATION: LNA-modifications at positions 1, 32

<400> SEQUENCE: 49
gctctgcagg ctagctacaa cgactagctc tc                                32

<210> SEQ ID NO 50
<211> LENGTH: 31
<212> TYPE: DNA
<213> ORGANISM: Artificial Sequence
<220> FEATURE:
<223> OTHER INFORMATION: Artificial DNAzyme with LNA modifications
<220> FEATURE:
<221> NAME/KEY: misc_feature
<222> LOCATION: (1)..(31)
<223> OTHER INFORMATION: LNA-modifications at positions 1, 31

<400> SEQUENCE: 50
gctctgcagg ctagctacaa cgactagctc t                                 31

<210> SEQ ID NO 51
<211> LENGTH: 30
<212> TYPE: DNA
<213> ORGANISM: Artificial Sequence
<220> FEATURE:
<223> OTHER INFORMATION: Artificial DNAzyme with LNA modifications
<220> FEATURE:
<221> NAME/KEY: misc_feature
<222> LOCATION: (1)..(30)
<223> OTHER INFORMATION: LNA-modifications at positions 1, 30

<400> SEQUENCE: 51
gctctgcagg ctagctacaa cgactagctc                                   30

<210> SEQ ID NO 52
<211> LENGTH: 30
<212> TYPE: DNA
<213> ORGANISM: Artificial Sequence
<220> FEATURE:
<223> OTHER INFORMATION: Artificial DNAzyme with LNA modifications
<220> FEATURE:
<221> NAME/KEY: misc_feature
<222> LOCATION: (1)..(30)
<223> OTHER INFORMATION: LNA-modifications at positions 1, 5, 26, 30

<400> SEQUENCE: 52
gctctgcagg ctagctacaa cgactagctc                                   30

<210> SEQ ID NO 53
<211> LENGTH: 19
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(19)
<223> OTHER INFORMATION: Phosphorothioate linkages
<220> FEATURE:
<221> NAME/KEY: misc_feature
<222> LOCATION: (1)..(19)
<223> OTHER INFORMATION: LNA-modifications at positions 1, 2, 3, 17, 18,
      and 19

<400> SEQUENCE: 53
tttgtgttct catgactga                                            19

<210> SEQ ID NO 54
<211> LENGTH: 18
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(18)
<223> OTHER INFORMATION: Phosphorothioate linkages
<220> FEATURE:
<221> NAME/KEY: misc_feature
<222> LOCATION: (1)..(18)
<223> OTHER INFORMATION: LNA-modifications at positions 1, 2, 3, 16, 17,
      and 18

<400> SEQUENCE: 54
ttgtgttctc atgactga                                             18

<210> SEQ ID NO 55
<211> LENGTH: 20
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(20)
<223> OTHER INFORMATION: Phosphorothioate linkages
<220> FEATURE:
<221> NAME/KEY: misc_feature
<222> LOCATION: (1)..(20)
<223> OTHER INFORMATION: LNA-modifications at positions 1, 2, 3, 18, 19
      and 20

<400> SEQUENCE: 55
atttgtgttc tcatgactga                                           20

<210> SEQ ID NO 56
<211> LENGTH: 20
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(20)
<223> OTHER INFORMATION: Phosphorothioate linkages
<220> FEATURE:
<221> NAME/KEY: misc_feature
<222> LOCATION: (1)..(20)
<223> OTHER INFORMATION: LNA-modifications at positions 1, 2, 3, 18, 19,
      and 20

<400> SEQUENCE: 56
tcacttcaat ttgtgttctc                                           20

<210> SEQ ID NO 57
<211> LENGTH: 19
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature

```
<222> LOCATION: (1)..(19)
<223> OTHER INFORMATION: Phosphorothioate linkages
<220> FEATURE:
<221> NAME/KEY: misc_feature
<222> LOCATION: (1)..(19)
<223> OTHER INFORMATION: LNA-modifications at positions 1, 2, 3, 17, 18,
      and 19

<400> SEQUENCE: 57
cacttcaatt tgtgttctc                                                19

<210> SEQ ID NO 58
<211> LENGTH: 19
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(19)
<223> OTHER INFORMATION: Phosphorothioate linkages
<220> FEATURE:
<221> NAME/KEY: misc_feature
<222> LOCATION: (1)..(19)
<223> OTHER INFORMATION: LNA-modifications at positions 1, 2, 3, 17, 18,
      and 19

<400> SEQUENCE: 58
tcacttcaat ttgtgttct                                                19

<210> SEQ ID NO 59
<211> LENGTH: 18
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(18)
<223> OTHER INFORMATION: Phosphorothioate linkages
<220> FEATURE:
<221> NAME/KEY: misc_feature
<222> LOCATION: (1)..(18)
<223> OTHER INFORMATION: LNA-modifications at positions 1, 2, 3, 16, 17,
      and 18

<400> SEQUENCE: 59
tcacttcaat ttgtgttc                                                 18

<210> SEQ ID NO 60
<211> LENGTH: 18
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(18)
<223> OTHER INFORMATION: Phosphorothioate linkages
<220> FEATURE:
<221> NAME/KEY: misc_feature
<222> LOCATION: (1)..(18)
<223> OTHER INFORMATION: LNA-modifications at positions 1, 2, 3, 16, 17,
      and 18

<400> SEQUENCE: 60
ttcaatttgt gttctcat                                                 18
```

```
<210> SEQ ID NO 61
<211> LENGTH: 21
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(21)
<223> OTHER INFORMATION: Phosphorothioate linkages
<220> FEATURE:
<221> NAME/KEY: misc_feature
<222> LOCATION: (1)..(21)
<223> OTHER INFORMATION: LNA-modifications at positions 1, 2, 3, 19, 20,
      and 21

<400> SEQUENCE: 61
tcacttcaat tgtgttctc a                                              21

<210> SEQ ID NO 62
<211> LENGTH: 18
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(18)
<223> OTHER INFORMATION: Phosphorothioate linkages
<220> FEATURE:
<221> NAME/KEY: misc_feature
<222> LOCATION: (1)..(18)
<223> OTHER INFORMATION: LNA-modifications at positions 1, 2, 3, 16, 17,
      and 18

<400> SEQUENCE: 62
atttgtgttc tcatgact                                                 18

<210> SEQ ID NO 63
<211> LENGTH: 21
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(21)
<223> OTHER INFORMATION: Phosphorothioate linkages
<220> FEATURE:
<221> NAME/KEY: misc_feature
<222> LOCATION: (1)..(21)
<223> OTHER INFORMATION: LNA-modifications at positions 1, 2, 3, 19, 20,
      and 21

<400> SEQUENCE: 63
nnnnnnnnnn nnnnnnnnnn n                                             21

<210> SEQ ID NO 64
<211> LENGTH: 21
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(21)
<223> OTHER INFORMATION: Phosphorothioate linkages
<220> FEATURE:
<221> NAME/KEY: misc_feature
```

```
<222> LOCATION: (1)..(21)
<223> OTHER INFORMATION: LNA-modifications at positions 1, 2, 3, 19, 20,
      and 21

<400> SEQUENCE: 64
nnnnnnnnnn nnnnnnnnnn n                                              21

<210> SEQ ID NO 65
<211> LENGTH: 19
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(19)
<223> OTHER INFORMATION: Phosphorothioate linkages
<220> FEATURE:
<221> NAME/KEY: misc_feature
<222> LOCATION: (1)..(19)
<223> OTHER INFORMATION: LNA-modifications at positions 1, 2, 3, 17, 18,
      and 19

<400> SEQUENCE: 65
nnnnnnnnnn nnnnnnnnn                                                 19

<210> SEQ ID NO 66
<211> LENGTH: 19
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(19)
<223> OTHER INFORMATION: Phosphorothioate linkages
<220> FEATURE:
<221> NAME/KEY: misc_feature
<222> LOCATION: (1)..(19)
<223> OTHER INFORMATION: LNA-modifications at positions 1, 2, 3, 18, and
      19

<400> SEQUENCE: 66
nnnnnnnnnn nnnnnnnnn                                                 19

<210> SEQ ID NO 67
<211> LENGTH: 20
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(20)
<223> OTHER INFORMATION: Phosphorothioate linkages
<220> FEATURE:
<221> NAME/KEY: misc_feature
<222> LOCATION: (1)..(20)
<223> OTHER INFORMATION: LNA-modifications at positions 1, 2, 3, 18, 19,
      and 20

<400> SEQUENCE: 67
nnnnnnnnnn nnnnnnnnnn                                                20

<210> SEQ ID NO 68
<211> LENGTH: 18
<212> TYPE: DNA
<213> ORGANISM: Artificial Sequence
```

```
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(18)
<223> OTHER INFORMATION: Phosphorothioate linkages
<220> FEATURE:
<221> NAME/KEY: misc_feature
<222> LOCATION: (1)..(18)
<223> OTHER INFORMATION: LNA-modifications at positions 1, 2, 3, 16, 17,
      and 18

<400> SEQUENCE: 68
nnnnnnnnnn nnnnnnnn                                                 18

<210> SEQ ID NO 69
<211> LENGTH: 20
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(20)
<223> OTHER INFORMATION: Phosphorothioate linkages
<220> FEATURE:
<221> NAME/KEY: misc_feature
<222> LOCATION: (1)..(20)
<223> OTHER INFORMATION: LNA-modifications at positions 1, 2, 3, 18, 19,
      and 20

<400> SEQUENCE: 69
nnnnnnnnnn nnnnnnnnnn                                               20

<210> SEQ ID NO 70
<211> LENGTH: 18
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(18)
<223> OTHER INFORMATION: Phosphorothioate linkages
<220> FEATURE:
<221> NAME/KEY: misc_feature
<222> LOCATION: (1)..(18)
<223> OTHER INFORMATION: LNA-modifications at positions 1, 2, 3, 16, 17,
      and 18

<400> SEQUENCE: 70
nnnnnnnnnn nnnnnnnn                                                 18

<210> SEQ ID NO 71
<211> LENGTH: 21
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(21)
<223> OTHER INFORMATION: Phosphorothioate linkages
<220> FEATURE:
<221> NAME/KEY: misc_feature
<222> LOCATION: (1)..(21)
<223> OTHER INFORMATION: LNA-modifications at positions 1, 2, 3, 19, 20,
      and 21
```

```
<400> SEQUENCE: 71
nnnnnnnnnn nnnnnnnnn n                                              21

<210> SEQ ID NO 72
<211> LENGTH: 20
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(20)
<223> OTHER INFORMATION: Phosphorothioate linkages
<220> FEATURE:
<221> NAME/KEY: misc_feature
<222> LOCATION: (1)..(20)
<223> OTHER INFORMATION: LNA-modifications at positions 1, 2, 3, 18, 19,
      and 20

<400> SEQUENCE: 72
nnnnnnnnnn nnnnnnnnnn                                               20

<210> SEQ ID NO 73
<211> LENGTH: 18
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(18)
<223> OTHER INFORMATION: Phosphorothioate linkages
<220> FEATURE:
<221> NAME/KEY: misc_feature
<222> LOCATION: (1)..(18)
<223> OTHER INFORMATION: LNA-modifications at positions 1, 2, 3, 16, 17,
      and 18

<400> SEQUENCE: 73
nnnnnnnnnn nnnnnnnn                                                 18

<210> SEQ ID NO 74
<211> LENGTH: 20
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
<221> NAME/KEY: misc_feature
<222> LOCATION: (1)..(20)
<223> OTHER INFORMATION: Phosphorothioate linkages
<220> FEATURE:
<221> NAME/KEY: misc_feature
<222> LOCATION: (1)..(20)
<223> OTHER INFORMATION: LNA-modifications at positions 1, 2, 3, 18, 19,
      and 20

<400> SEQUENCE: 74
nnnnnnnnnn nnnnnnnnnn                                               20

<210> SEQ ID NO 75
<211> LENGTH: 20
<212> TYPE: DNA
<213> ORGANISM: Artificial Sequence
<220> FEATURE:
<223> OTHER INFORMATION: Artificial antisense construct with LNA
      modifications and phosphorothioate linkages
<220> FEATURE:
```

```
<221> NAME/KEY: misc_feature
<222> LOCATION: (1)..(20)
<223> OTHER INFORMATION: Phosphorothioate linkages
<220> FEATURE:
<221> NAME/KEY: misc_feature
<222> LOCATION: (1)..(20)
<223> OTHER INFORMATION: LNA-modifications at positions 1, 2, 3, 18, 19,
      and 20

<400> SEQUENCE: 75
nnnnnnnnnn nnnnnnnnnn                                              20

<210> SEQ ID NO 76
<211> LENGTH: 33
<212> TYPE: DNA
<213> ORGANISM: Artificial Sequence
<220> FEATURE:
<223> OTHER INFORMATION: Artificial DNAzyme

<400> SEQUENCE: 76
tcacttcaag gctagctaca acgattgtgt tct                               33

<210> SEQ ID NO 77
<211> LENGTH: 31
<212> TYPE: DNA
<213> ORGANISM: Artificial Sequence
<220> FEATURE:
<223> OTHER INFORMATION: Artificial DNAzyme

<400> SEQUENCE: 77
ttgtgttctc aggctagcta caacgagact g                                 31

<210> SEQ ID NO 78
<211> LENGTH: 33
<212> TYPE: DNA
<213> ORGANISM: Artificial Sequence
<220> FEATURE:
<223> OTHER INFORMATION: Artificial DNAzyme

<400> SEQUENCE: 78
ttctcatgag gctagctaca acgatgagcc ttg                               33

<210> SEQ ID NO 79
<211> LENGTH: 33
<212> TYPE: DNA
<213> ORGANISM: Artificial Sequence
<220> FEATURE:
<223> OTHER INFORMATION: Artificial DNAzyme

<400> SEQUENCE: 79
agctctgcag gctagctaca acgactagct ctc                               33

<210> SEQ ID NO 80
<211> LENGTH: 36
<212> TYPE: DNA
<213> ORGANISM: Homo sapiens

<400> SEQUENCE: 80
aaggctcagt catgagaaca caaattgaag tgatcc                            36
```

APPROACH FOR TREATING INFLAMMATORY DISORDERS

CROSS-REFERENCE TO RELATED APPLICATIONS

This application is a U.S. national stage of International Patent Application No. PCT/EP2017/054374, filed Feb. 24, 2017, which is entitled to priority under 35 U.S.C. § 119(e) to European Patent Application 16002305.7, filed Oct. 27, 2016, and European Patent Application 16000468.5, filed Feb. 26, 2016, which are incorporated herein by reference in their entirety.

The Sequence Listing for this application is labeled "103270.000038_Sequence listing_August2019", which was created on Aug. 19, 2019, and is 37 KB. The entire content is incorporated herein by reference in its entirety.

FIELD OF THE INVENTION

The present invention relates to a novel approach for treating inflammatory disorders and other diseases, which is based on targeting ROR gamma t mRNA. The invention is directed to oligonucleotides comprising 10 to 22 modified or unmodified nucleotides complementary to specifically selected regions of the RORC, transcript variant 2 mRNA (RORC2), which codes for the ROR gamma t protein.

BACKGROUND OF THE INVENTION

Th17 cells are a subset of T helper cells which have been associated with several chronic inflammatory and autoimmune diseases. Upon polarization and activation Th17 cells produce highly proinflammatory molecules like cytokines IL-17A, IL-17F, IL-21, IL-22 and chemokines CXCL8 and CCL20. Furthermore, Th17 cells produce effector molecules like GM-CSF as well as provide help to B cells, induce germinal center formation and class switching.

The effector mechanisms and exacerbating Th17 responses are associated with the pathogenesis of acute and chronic inflammatory diseases like psoriasis, rheumatoid arthritis (RA), multiple sclerosis (MS), systemic lupus erythematosus (SLE), diverse phenotypes of inflammatory bowel diseases (IBD), asthma and allergy.

In rheumatoid arthritis the role of the Th17 has been confirmed in several mouse models as well as in patient's material. High frequency of IL17 producing cells has been found in diseased synovium, and intra-articular administration of IL17 in collagen-induced arthritis models has led to worsening of RA symptoms. Furthermore, IL17RA deficient mice develop only very mild forms of RA. To date, anti-IL17A and anti-IL17RA monoclonal antibodies have been shown protective from progressive RA in humans and are approved as therapeutics.

In psoriasis, psoriatic arthritis as well as plaque psoriasis, chronic activation of Th17 cells and pro-inflammatory response against skin autoantigens as well as skin microbiota is the major cause of pathology. Respective patients' skin biopsies show high levels of IL17, IL23, IL6 and IL12, which represent the proinflammatory mixed Th1/Th17 phenotype. Additionally, Th17 cells in psoriatic plaques produce CCL20 and recruit more Th17, mast cells & neutrophils to prolong and elevate the response. Further, Th17 plays a role in inflammation processes that are part of several other skin phenotypes like acne, dermatomyositis and scleroderma.

Beside the skin diseases, Th17 cells play also an important role in further mucocutaneous inflammatory diseases such as chronic, allergic and steroid-resistant asthma, chronic obstructive pulmonary disease (COPD) and inflammatory bowel diseases, like Crohn's disease, enteritis and ulcerative colitis. IL17A has been found in high levels in sputum of severe asthma patients as well as of COPD patients. IL17 is potently induced via aryl-hydrocarbon receptor (AhR), a target of cigarette smoke ingredients and several pollutants.

The pathology of IBD is an intensively studied field and convincing data, despite diversity of models used, show the importance of Th17 cells. In Crohn's disease patients experience reoccurring disease phases with increased Th17 frequencies. The strong Th17-driven autoimmune response might be linked to the IL23R polymorphism, and the overshooting host defense against gut microbiota is based on a multiplicity of Th17-mediated mechanisms. Nevertheless, the inhibition of IL17 was not shown beneficial in Crohn's disease, which mirrors the diversity of IBD phenotypes in the patient population.

One of the first diseases that was shown to be Th17-driven was multiple sclerosis and although the complexity of the disease increases, Th17 cells still remain in the central role. Diverse cell types from the brain biopsies of MS patients showed IL17A overexpression and extensive infiltration of lymphocytes. Furthermore, the peripheral phenotype of MS seems also to be Th17-dependent, as these cells have been shown to provide B cell help and may induce autoantibody production.

As in MS, similar involvement of Th17 cells has been shown in another autoimmune phenotype—systemic lupus erythematosus ("SLE"). This complex and diverse disease worsens with increase of Th17 cell numbers. Major effect of Th17 in SLE was observed in progressive vasculitis and endothelial dysfunction. This effect is not only characteristic to SLE, but also to Behcet's disease, uveitis and Sjögren syndrome. IL17-producing cells have been found to accumulate in vessel walls of autoimmune vasculitis patients and recruit other proinflammatory cells, like neutrophils and macrophages. IL17 has prothrombic and procoagulant effects on human endothelial cells.

Concomitantly with accumulation of Th17 in vasculitis there is a positive correlation between Th17 frequency and frequency of aortic lesions in coronary atherosclerosis. Here, increase in Th17 levels lead to increase in size of aortic lesions and frequency of cardiac infarction.

Beside rheumatoid arthritis, Th17 plays a role in another chronic inflammatory joint and spine disease, Morbus Bechterew. Here, during ongoing tendon inflammation Th17 and mast cells both produce IL17 in the synovium and drive ectopic bone formation and joint stiffness. The ongoing inflammation is fairly treatable with anti-TNF alpha therapy but the bone reformation and ankyloses might be Th17 dependent.

One yet partially explored field of Th17 cells is neuropathic pain. There is accumulating data that diverse neuropathic and chronic unspecific low back pain correlate with the disrupted balance between Th17 and regulatory T cells.

Taken together, inhibition of Th17 development and function appears to clearly be a promising target for the treatment of the above-mentioned diseases.

The master transcription factor of Th17 cells is ROR gamma t. Retinoic acid receptor-related orphan receptors (RORs) are members of the steroid hormone nuclear receptor family. The ROR transcription factor subfamily consists of three members: ROR alpha (RORA), ROR beta (RORB) and ROR gamma (RORC). Each member is expressed as independent gene and binds as monomer to genomic response elements. Through alternative splicing and differential promoter usage each ROR member generates variants that have different tissue expression patterns and that regulate different targets. RORC has two isoforms that arise from differential promoter usage and that differ in the first exon. These two transcript variants are annotated as: NM_005060 for ROR gamma (RORC1) and NM_001001523 for ROR gamma t (RORC2). While ROR gamma is expressed in a variety of tissues either constitutively or under circadian rhythm, ROR gamma t expression is limited to the cells of the immune system. The highest expression of ROR gamma was shown for skeletal muscle, kidney and liver while ROR gamma t expression peaks in the developing double positive thymocytes, T helper lineage 17 cells (Th17), lymphoid-tissue inducer cells (LTi) and several intraepithelial lymphoid cell (ILCs) subpopulations. ROR gamma t has a critical role in thymopoiesis as it reduces Fas expression and IL2 dependency, rescuing the thymocytes from the activation-induced cell death during thymic selection. Further, ROR gamma t is important for the function of LTis and development of secondary lymphoid tissues.

Thus, inhibition of Th17 development and function through the inhibition of the master differentiation factor, ROR gamma t, appears to be a viable option.

One possible approach for inhibiting the Th17-driven pathologies is to inhibit the effector functions of already present Th17 as well as interfere with the new differentiation of nave T cells towards Th17 lineage by blocking ROR gamma t. However, ROR gamma t is an intracellular molecule and cannot be reached by therapeutic antibodies. Furthermore, the currently available ROR gamma and gamma t small molecule antagonists target the ligand or DNA binding domains that are identical between the both molecules. As previously stated, ROR gamma is ubiquitously expressed and has roles in many central physiological processes. The most studied role of ROR gamma is the circadian regulation of lipid and sugar metabolism in liver and skeletal muscle. The absence of ROR gamma leads to imbalance of liver metabolic function, metabolic syndrome, insulin resistance and obesity. Additionally, several studies have evidenced an important role of ROR gamma in cancer. ROR gamma deficiency in mice leads to a high incidence of thymic lymphomas with frequent liver and spleen metastasis. Thus, there is a high an unmet need for ROR gamma t-specific inhibitors.

One alternative approach for inhibiting the Th17-driven pathologies is to knock down the expression of ROR gamma t on the nucleic acid level. Such targeting has several important advantages, since in comparison with the available small molecule therapeutics, targeting on the nucleic acid level may be adjusted to target the ROR gamma t transcript exclusively, thus having no effects on ROR gamma. Small molecules currently in development do not have this level of specificity which may lead to adverse side-effects with these drug candidates. However, the initial approach of using DNAzymes based on the 10-23 motif, which had already been successfully applied to the inhibition of GATA-3 (see WO 2005/033314) did not result in an inhibition of the expression of RORC2 relative to untreated control in HDLM2 cells by at least 50% (see Example 2).

WO 2006/007486 is based on examining the influence of RORC2 expression on the proliferation of immune cells and claims the use of inhibitors or antagonists of RORC2 expression. Antisense constructs are listed as potential inhibitors, but no working examples are shown.

WO 2012/129394 relates to the treatment of cancer by using IL-9-receptor agonists wherein the agonists can act either directly on the receptor or indirectly by regulating RORC2 expression. Antisense constructs are listed as potential inhibitors, but no working examples are shown.

CN 102 732 562 apparently describes siRNA-based inhibition of, for example, RORC1, including siRNA constructs according to SEQ ID NOs: 7 bis 9. No siRNA constructs against RORC2 appear to be shown.

WO 2011/113015 relates to the use of anti-sense constructs against nuclear hormone receptors ("NHRs"). While RORC1 is listed as an example of such NHRs, RORC2 is not listed.

Hakemi et al.; Avicenna Journal of Medical Biotechnology 5 (2013) 10-19, relates to the siRNA-based gene silencing of RORC2, showing in total three anti-RORC2 siRNA constructs (see Table 3). These constructs, however, do not appear to be RORC2-specific since they correspond to regions of RORC2 that are shared with RORC1 (start positions 872, 1197, and 1303, respectively, of SEQ ID NO: 1 shown herein in FIG. 1).

Burgler et al., J. Immunol. 184 (2010) 6161-6169 examines the interaction of RORC2 with the FOXP3 promotor, including the use of two siRNA constructs in the knock-down of RORC2 (see Supplemental table 4). These constructs, however, do not appear to be RORC2-specific since they correspond to regions of RORC2 that are shared with RORC1 (start positions 875 and 2473, respectively, of SEQ ID NO: 1 shown herein in FIG. 1).

Webering "Zur Rolle des α-Melanozyten-stimulierenden Hormons (α-MSH) and des retinoid-related orphan receptor γt (RORγt) bei der Immunpathogenese des Asthma bronchiale", PhD thesis, Lübeck 2014; Kategorie "Y") relates to the role of RORC2 in the immune pathogenesis of asthma bronchiale, including the use of DNAzymes and of three different siRNA constructs for inhibiting RORγt expression. While the use of DNAzymes could not be shown to have any influence on RORγt expression (see Section 3.2.3 and FIG. 36), siRNA constructs apparently resulted in a reduction of RORγt expression by up to 65% after 48 h (see Section 3.2.4 and FIG. 38). However, it is unclear which regions of RORγt were targeted, since the sequences shown in Table 5 do not match with the RORC2 sequence shown as SEQ ID NO: 1 herein in FIG. 1.

WO 2004/024879 relates to the interaction of RORs with the p21 pathway. In total, DNA sequences are shown for 15 different RORs, apparently including RORC2 (SEQ ID NO: 12). For three of those RORs, but not for RORC2, siRNA-based knock-down experiments are shown.

Lin et al., Mediators Inflamm. 2015: 290657 and Song et al., Biochem. Biophys. Res. Commun. 452 (2014) 1040-1045, relate to the inhibition of RORC2 with small molecules and aptamer-siRNA-chimerae. No sequence information is apparently given.

Thus, therapeutic agents which are able to specifically inhibit the expression of ROR gamma t intracellularly are essential for the treatment of Th17-driven diseases, in particular inflammatory disorders of various organs. Hence, there is still a high scientific and medical need for therapeutic agents, which reduce or inhibit RORC2 expression and/or activity. Particularly, there is a longstanding need for oligonucleotides, which specifically interact and thus, reduce or inhibit the expression of RORC2, as well as oligonucleotides, which specifically inhibit RORC2, without causing any (severe) side effects.

SUMMARY OF THE INVENTION

Despite the negative results obtained with a DNAzyme based approach, the present inventors surprisingly identified that a rather similar approach of using certain antisense constructs was able to achieve the inhibition of the expression of RORC2 relative to untreated control in HDLM2 cells by at least 50%, with several candidates achieving inhibition of at least 80%, more particularly of at least 90%. This finding was unexpected and neither taught nor suggested by the prior art.

Thus, in a first aspect, the present invention relates to an oligonucleotide consisting of from 10 to 20 nucleotides, particularly from 15 to 18 nucleotides, wherein the sequence of said oligonucleotide corresponds to the antisense strand of the RORC2 nucleic acid coding sequence of SEQ ID NO. 1, wherein one or more nucleotide(s) of the oligonucleotide is/are optionally modified, and wherein said oligonucleotide inhibits the expression of RORC2 relative to untreated control in HDLM2 cells by at least 50%.

In an alternative first aspect, the present invention relates to an oligonucleotide consisting of from 10 to 22 nucleotides, particularly from 14 to 21 nucleotides, particularly from 15 to 21 nucleotides, and more particularly from 15 to 20 nucleotides, wherein the sequence of said oligonucleotide corresponds to the antisense strand of the RORC2 nucleic acid coding sequence of SEQ ID NO. 1, wherein one or more nucleotide(s) of the oligonucleotide is/are optionally modified, and wherein said oligonucleotide inhibits the expression of RORC2 relative to untreated control in HDLM2 cells by at least 50%.

In a second aspect, the present invention relates to a pharmaceutical composition comprising the oligonucleotide according to the present invention.

In a third aspect, the present invention relates to the oligonucleotides or the pharmaceutical composition according to the present invention for use in a method of preventing and/or treating a disease or disorder selected from the list of: an acute inflammatory disease, a chronic inflammatory disease, a neurodegenerative disease, a malignant tumor, and a benign tumor.

In a fourth aspect, the present invention relates to a method of preventing and/or treating a disease or disorder selected from the list of: an acute inflammatory disease, a chronic inflammatory disease, a neurodegenerative disease, a malignant tumor, and a benign tumor, comprising the step of administering an oligonucleotide of to the present invention or the pharmaceutical composition of to the present invention to a patient in need thereof

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 1 shows the complete RORC, transcript variant 2 mRNA (NM_001001523.1). In capital letters, the region unique to RORC2 (ROR gamma t) and not shared with RORC1 is given. Given that at least 3 mismatches to RORC1 are required, the usable space for 17 mer oligonucleotides specific for only RORC2 is indicated in bold letters. Bioinformatic screening was performed within this area in order to preserve specificity of oligonucleotides to only RORC2.

DETAILED DESCRIPTION OF THE INVENTION

Figure 2A:
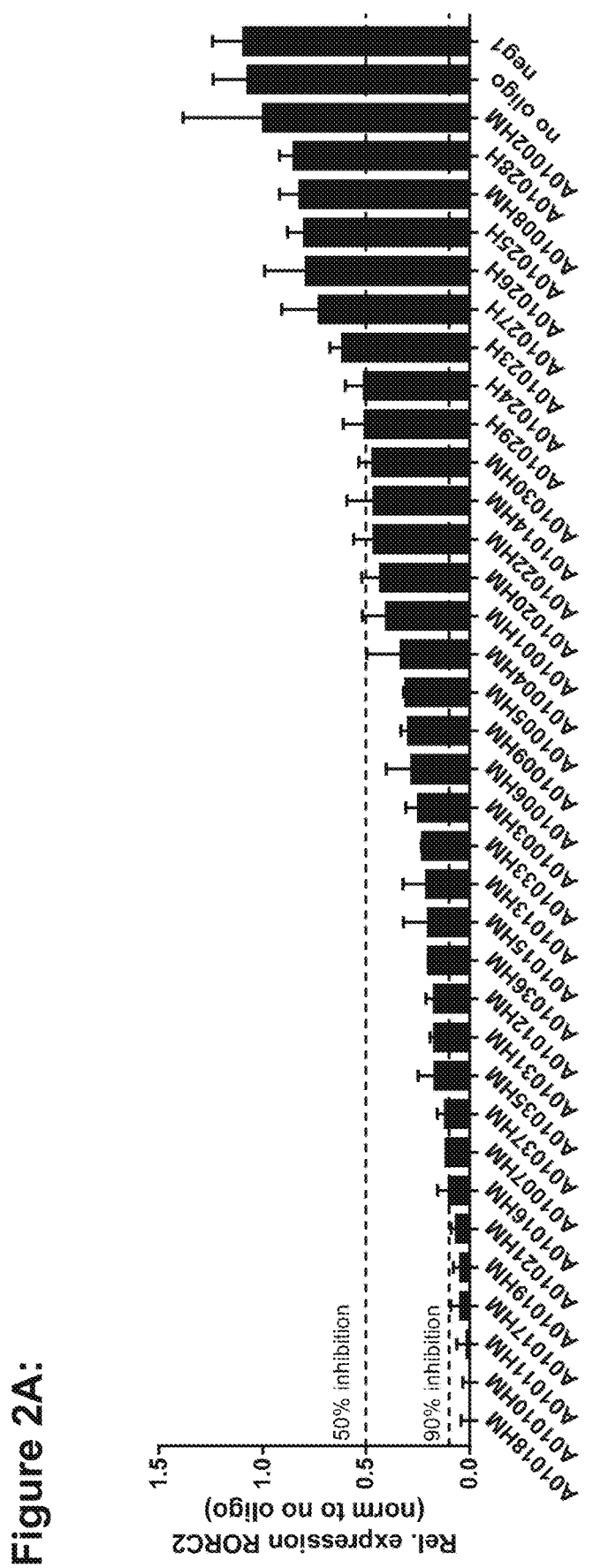
FIG. 2A shows the result of a first oligonucleotide screen for ROR gamma t inhibition in HDLM2 cells, as described in Example 2.

Thus, in a first aspect, the present invention relates to an oligonucleotide consisting of from 10 to 20 nucleotides, particularly from 15 to 18 nucleotides, wherein the sequence of said oligonucleotide corresponds to the antisense strand of the RORC2 nucleic acid coding sequence of SEQ ID NO. 1, wherein one or more nucleotide(s) of the oligonucleotide is/are optionally modified, and wherein said oligonucleotide inhibits the expression of RORC2 relative to untreated control in HDLM2 cells by at least 50%.

In an alternative first aspect, the present invention relates to an oligonucleotide consisting of from 10 to 22 nucleotides, particularly from 15 to 21 nucleotides, more particularly from 15 to 20 nucleotides, wherein the sequence of said oligonucleotide corresponds to the antisense strand of the RORC2 nucleic acid coding sequence of SEQ ID NO. 1, wherein one or more nucleotide(s) of the oligonucleotide is/are optionally modified, and wherein said oligonucleotide inhibits the expression of RORC2 relative to untreated control in HDLM2 cells by at least 50%.

In particular embodiments, the sequence of said oligonucleotide is complementary to a sequence comprised in the 5'-terminal part of the RORC2 nucleic acid coding sequence of SEQ ID NO. 1, wherein said 5'-terminal part consists of nucleotides 1 to 166, particularly of nucleotides 1 to 163, more particularly of nucleotides 1 to 162, provided that in each case at least three nucleotides of said oligonucleotide are complementary to nucleotides comprised in positions 1 to 148 of the RORC2 nucleic acid coding sequence of SEQ ID NO. 1.

In more particular embodiments, the sequence of said oligonucleotide is complementary to a sequence comprised in the 5'-terminal part of the RORC2 nucleic acid coding sequence of SEQ ID NO. 1, wherein said 5'-terminal part consists of nucleotides 131 to 166, particularly of nucleotides 131 to 163, more particularly of nucleotides 131 to 162, provided that in each case at least three nucleotides of said oligonucleotide are complementary to nucleotides comprised in positions 131 to 148 of the RORC2 nucleic acid coding sequence of SEQ ID NO. 1.

In particular embodiments, the sequence of said oligonucleotide comprises the sequence GTGTT, which is complementary to positions 147 to 151 of the RORC2 nucleic acid coding sequence of SEQ ID NO. 1. In more particular embodiments, the sequence of said oligonucleotide comprises the sequence GTGTTC, which is complementary to positions 146 to 151 of the RORC2 nucleic acid coding sequence of SEQ ID NO. 1. In more particular other embodiments, the sequence of said oligonucleotide comprises the sequence GTGTTCT, which is complementary to positions 145 to 151 of the RORC2 nucleic acid coding sequence of SEQ ID NO. 1. In particular other embodiments, the sequence of said oligonucleotide comprises the sequence TGTGTTCT, which is complementary to positions 145 to 152 of the RORC2 nucleic acid coding sequence of SEQ ID NO. 1. In particular other embodiments, the sequence of said oligonucleotide comprises the sequence TTGTGTTCT, which is complementary to positions 145 to 153 of the RORC2 nucleic acid coding sequence of SEQ ID NO. 1.

In particular embodiments of the present in invention, said oligonucleotide inhibits the expression of RORC2 relative to untreated control in HDLM2 cells by at least 75%, particularly by at least 80%, more particularly by at least 85%, more particularly by at least 90%.

In certain embodiments said oligonucleotide inhibits the expression of RORC2 relative to untreated control in HDLM2 cells by about 95%.

In the context of the present invention, the inhibition of expression of RORC2 is determined in accordance with the method shown in Example 2 or Example 3 below.

In particular embodiments of the present in invention, one or more nucleotide(s) in said oligonucleotide are modified.

Figure 3:
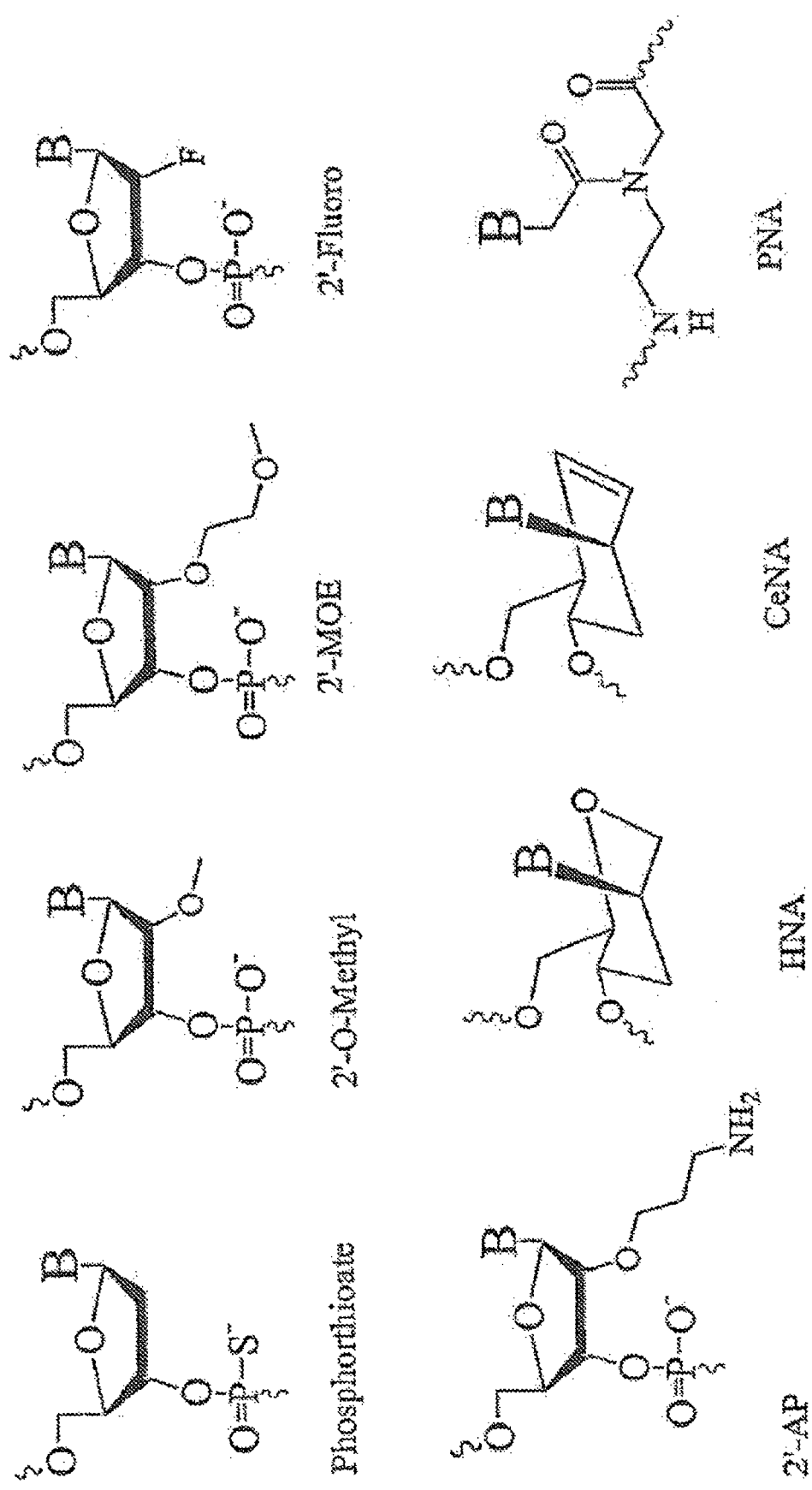
FIG. 3 shows a number of different modified nucleotides that may be used in the context of the present invention.
Figure 3:
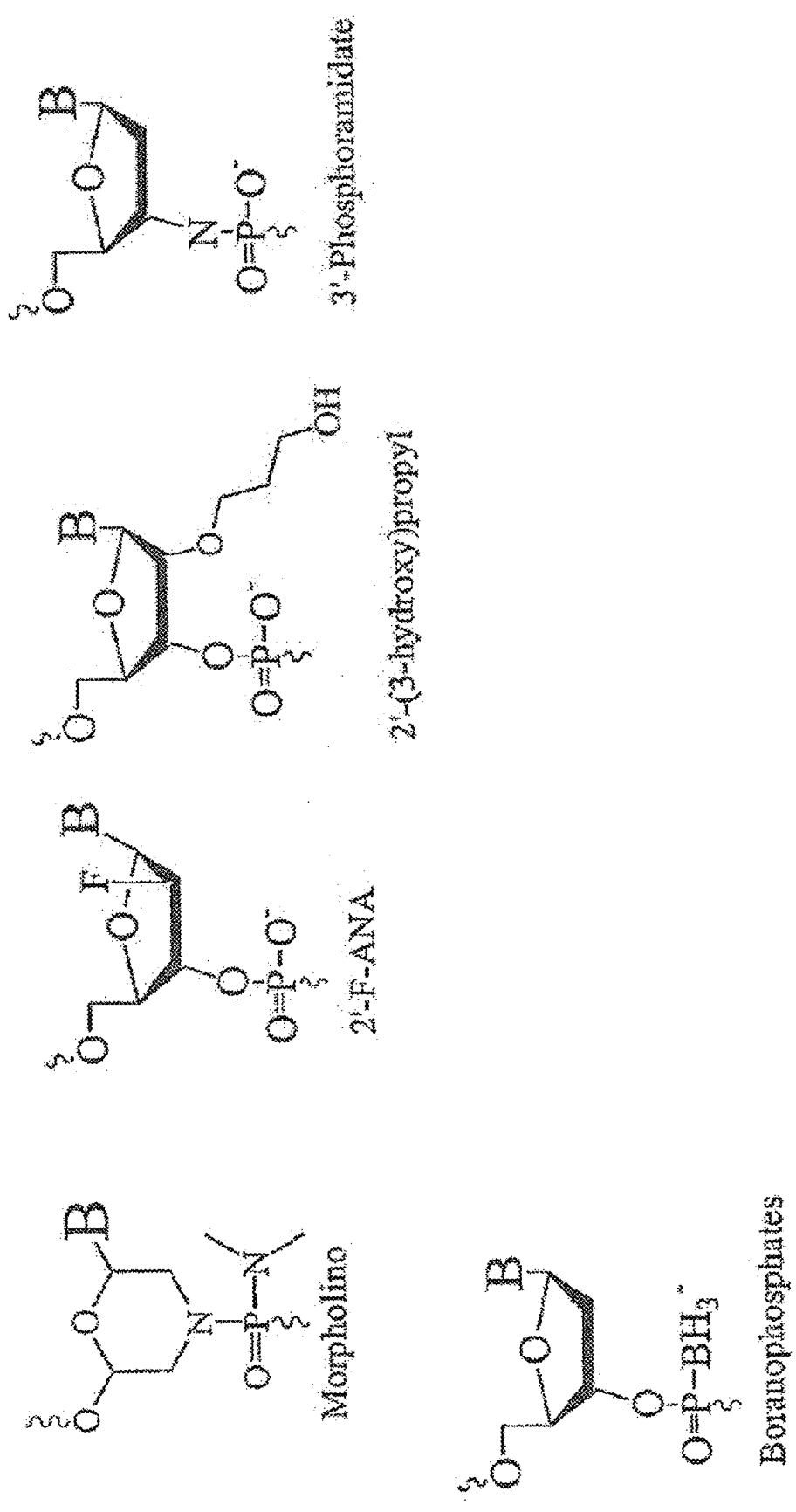
Figure 3:
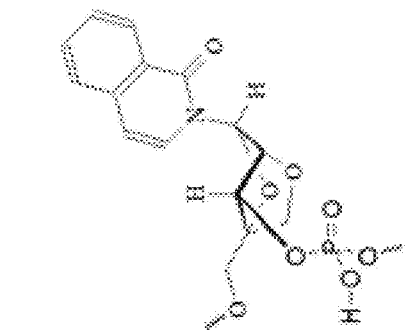
Figure 3:
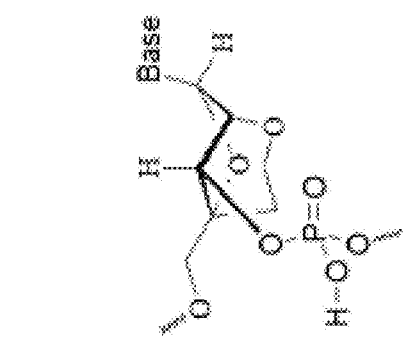
Figure 3:
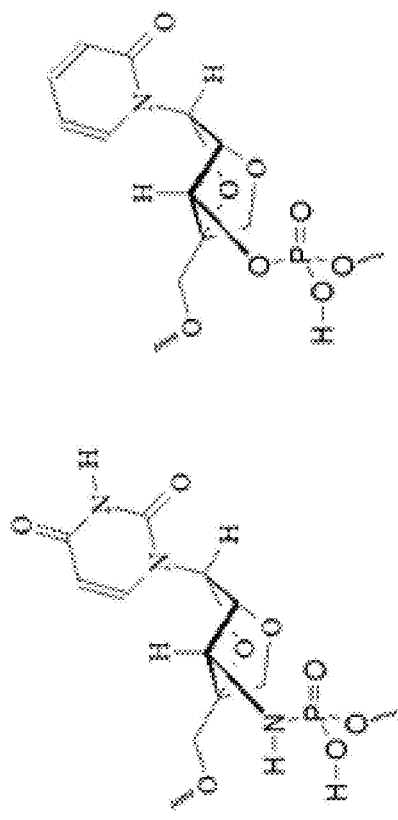
Figure 3:
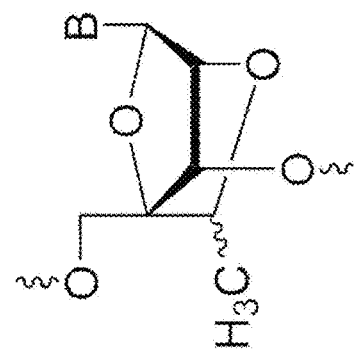

A nucleotide forms the building block of an oligonucleotide, and is for example composed of a nucleobase (nitrogenous base, e.g., purine or pyrimidine), a five-carbon sugar (e.g., ribose, 2-deoxyribose, arabinose, xylose, lyxose, allose, altrose, glucose, mannose, gulose, idose, galactose, talose or stabilized modifications of those sugars), and one or more phosphate groups. Examples of modified phosphate groups are phosphorothioate or methylphosphonate. Each compound of the nucleotide is modifiable, and is naturally or non-naturally occurring. Examples of the latter are: locked nucleic acid (LNA), 2', 4' constrained ethyl nucleic acids (c-ET), 2'-0,4'-C-ethylene-bridged nucleic acid (ENA), polyalkylene oxide—(such as triethylene glycol (TEG)), 2'-fluoro-, 2'-deoxy-2'-fluoro-beta-D-arabinonucleic acid (FANA), 2'-0-methoxy- and 2'-O-methyl-modified nucleotides. FIG. 3 shows examples of a number of different modified nucleotides that may be used in the context of the present invention.

An "LNA" is a modified RNA nucleotide, wherein the ribose moiety is modified with an extra bridge connecting the 2' oxygen and 4' carbon (2'-4'-ribonucleoside). The bridge locks the ribose in the 3'-endo (North) conformation, which is often found in the A-form duplexes. LNA nucleosides and nucleotides, respectively, comprise for example the forms of thio-LNA, oxy-LNA, or amino-LNA, in alpha-D- or beta-L-configuration, and can be mixed or combined, respectively, with DNA or RNA residues in the oligonucleotide.

A "bridged nucleic acid" is modified RNA nucleotide, sometimes also referred to as constrained or inaccessible RNA molecule, which may contain a five-membered, six-membered or even a seven-membered bridged structure with a "fixed" C3'-endo sugar puckering. The bridge is synthetically incorporated at the 2', 4'-position of the ribose to afford a 2', 4'-BNA monomer. Specific examples are "ENA" nucleotides, wherein the bridge is an ethylene bridge. FIG. 3 shows a number of BNA nucleotides that may be used in the context of the present invention.

In a particular embodiment, one or more nucleotide(s) in said oligonucleotide are modified, wherein the modified nucleotide contains a modified phosphate groups, particularly selected from a phosphorothioate and a methylphosphonate, particularly a phosphorothioate. In particular embodiments, all phosphate groups of the oligonucleotide are modified phosphate groups, particularly independently selected from phosphorothioates and methylphosphonates, particularly wherein all phosphate groups are phosphorothioates.

In particular embodiments, all nucleotides of the oligonucleotides of the present invention are linked by a phosphorothioate group.

In a particular embodiment, one or more nucleotide(s) in said oligonucleotide are modified, wherein the modified nucleotide is an LNA, a c-ET, an ENA, a polyalkylene oxide-, a 2'-fluoro-, a 2'-O-methoxy-, a FANA and/or a 2'-O-methyl-modified nucleotide.

In particular embodiments, the modified nucleotide(s) is/are located within the stretch of 5 nucleotides at the 5'- and/or 3'-end of the oligonucleotide, particularly at the 5'- and/or 3'-end of the oligonucleotide.

In particular embodiments, the oligonucleotides of the present invention comprise at least one modified nucleotide, particularly at least one LNA, c-ET and/or ENA, at the 5'- and/or 3'-end of the oligonucleotide. In a particular embodiment, the oligonucleotide comprises 1, 2, 3, or 4 LNAs or c-ETs or ENAs within the stretch of up to 5 nucleotides at the 5'-end, and 1, 2, 3, or 4 LNAs or c-ETs or ENAs within the stretch of up to 5 nucleotides at the 3'-end. In another particular embodiment, the oligonucleotide comprises 1, 2, 3, or 4 LNAs, c-ETs, or ENAs at the within the stretch of 5 nucleotides 5'-end or 3'-end, and a polyalkylene oxide such as TEG within the stretch of 5 nucleotides at the 3'- or 5'-end.

In particular embodiments, said oligonucleotide is a Gapmer comprising at least one LNA nucleotide within the stretch of 5 nucleotides at the 5'-end of said oligonucleotide, and at least one LNA nucleotide within the stretch of 5 nucleotides at the 3'-end of said oligonucleotide. In particular embodiments, said Gapmer comprises 2 or 3 LNA nucleotides within the stretch of 5 nucleotides at the 5'-end of said oligonucleotide, and 2 or 3 LNA nucleotides within the stretch of 5 nucleotides at the 3'-end of said oligonucleotide.

In the context of the present invention, the term "Gapmer" refers to a chimeric antisense oligonucleotide that contains a central block of deoxynucleotide monomers sufficiently long to induce RNase H cleavage. The central block of a Gapmer is flanked by blocks of 2'-O modified ribonucleotides or other artificially modified ribonucleotide monomers such as bridged nucleic acids (BNAs) that protect the internal block from nuclease degradation. In many earlier studies modified DNA analogs were investigated for their stability in biological fluids. In the majority of these experiments phosphorothioate DNA analogs were used. More recently, several types of artificial nucleotide monomers including BNA monomers have been investigated for their usefulness in the design of Gapmers. Gapmers have been used to obtain RNase-H mediated cleavage of target RNAs, while reducing the number of phosphorothioate linkages. Phosphorothioates possess increased resistance to nucleases compared to unmodified DNA. However, they have several disadvantages. These include low binding capacity to complementary nucleic acids and non-specific binding to proteins that cause toxic side-effects limiting their applications. The occurrence of toxic side-effects together with non-specific binding causing off-target effects has stimulated the design of new artificial nucleic acids for the development of modified oligonucleotides that provide efficient and specific antisense activity in vivo without exhibiting toxic side-effects.

LNA Gapmers are powerful tools for loss of function studies of proteins, mRNA and lncRNAs. These single strand antisense oligonucleotides catalyze RNase H-dependent degradation of complementary RNA targets. LNA Gapmers are typically 12-20 nucleotides long enriched with LNA in the flanking regions and DNA in a LNA free central gap—hence the name Gapmer. The LNA-containing flanking regions confers nuclease resistance to the antisense oligo while at the same time increases target binding affinity regardless of the GC content. The central DNA "gap" activates RNase H cleavage of the target RNA upon binding.

In particular embodiments of the present in invention, the oligonucleotide comprises a sequence selected from the group consisting of SEQ ID NO. 2 to SEQ ID NO. 34 and SEQ ID NO. 53 to SEQ ID NO. 74; particularly from the group consisting of SEQ ID NO. 2 to SEQ ID NO. 4, SEQ ID NO. 6 to SEQ ID NO. 27, SEQ ID NO. 31 to SEQ ID NO. 34 and SEQ ID NO. 53 to SEQ ID NO. 74; particularly from the group consisting of SEQ ID NO. 2 to SEQ ID NO. 4, SEQ ID NO. 6 to SEQ ID NO. 12, SEQ ID NO. 14, SEQ ID NO. 15, SEQ ID NO. 17, SEQ ID NO. 23 to SEQ ID NO. 27, and SEQ ID NO. 53 to SEQ ID NO. 64; more particularly from the group consisting of SEQ ID NO. 2 to SEQ ID NO. 4, SEQ ID NO. 6 to SEQ ID NO. 11, SEQ ID NO. 23 to SEQ ID NO. 26, and SEQ ID NO. 53 to SEQ ID NO. 62; more particularly from the group consisting of SEQ ID NO. 2 to SEQ ID NO. 4, SEQ ID NO. 6 to SEQ ID NO. 9, SEQ ID NO. 23, and SEQ ID NO. 53 to SEQ ID NO. 59; and more particularly from the group consisting of SEQ ID NO. 2 to SEQ ID NO. 4, SEQ ID NO. 6, SEQ ID NO. 7 and SEQ ID NO. 53 to SEQ ID NO. 55.

In certain embodiments of the present in invention, the oligonucleotide comprises a sequence selected from the group consisting of SEQ ID NO. 2 and SEQ ID NO. 3.

In a particular embodiment, the oligonucleotide is a variant of a sequence selected from the group consisting of SEQ ID NO. 2 to SEQ ID NO. 34 and SEQ ID NO. 53 to SEQ ID NO. 74, wherein in such variant one or more of the phosphorothioates are independently replaced by an unmodified phosphate of a modified phosphate other than a phosphorothioate, particularly a methylphosphonate.

In a particular embodiment, the oligonucleotide is a variant of a sequence selected from the group consisting of SEQ ID NO. 2 to SEQ ID NO. 34 and SEQ ID NO. 53 to SEQ ID NO. 74, wherein such variant comprises one or more nucleotide mismatches particularly one or two mismatches, more particularly one mismatch, provided that any such variant including the mismatch(es), when analysed with the bioinformatic tools described in Example 1, contains at least one mismatch relative to human whole genome screening while maintaining homology to relevant species.

In a second aspect, the present invention relates to a pharmaceutical composition comprising an oligonucleotide according to the present invention.

In particular embodiments, the pharmaceutical composition further comprises a pharmaceutically acceptable carrier.

In particular embodiments, the pharmaceutical composition further comprises at least one additional component selected from: a further anti-sense compound, an antibody, a chemotherapeutic compound, an anti-inflammatory compound, an antiviral compound, an immuno-modulating compound, a pharmaceutically acceptable binding agents and an adjuvant.

In one embodiment, the oligonucleotide and the pharmaceutical composition, respectively, is formulated as dosage unit in form of capsules, tablets and pills etc., respectively, which contain for example the following compounds: microcrystalline cellulose, gum or gelatin as binders; starch or lactose as excipients; stearates as lubricants, various sweetening or flavouring agents. For capsules the dosage unit may contain a liquid carrier like fatty oils. Likewise coatings of sugar or enteric agents may be part of the dosage unit.

The oligonucleotide and/or the pharmaceutical composition is administrable via different routes. These routes of administration include, but are not limited to, electroporation, epidermal, impression into skin, intra-arterial, intra-articular, intracranial, intradermal, intra-lesional, intra-muscular, intranasal, intra-ocular, intrathecal, intracameral, intraperitoneal, intraprostatic, intrapulmonary, intraspinal, intratracheal, intratumoral, intravenous, intravesical, placement within cavities of the body, nasal inhalation, oral, pulmonary inhalation (e.g., by inhalation or insufflation of powders or aerosols, including by nebulizer), subcutaneous, subdermal, topical (including ophthalmic and to mucous membranes including vaginal and rectal delivery), or transdermal administration.

For parenteral, subcutaneous, intradermal or topical administration the oligonucleotide and/or the pharmaceutical composition include for example a sterile diluent, buffers, regulators of toxicity and antibacterials. In a preferred embodiment, the oligonucleotide or pharmaceutical composition is prepared with carriers that protect against degradation or immediate elimination from the body, including implants or microcapsules with controlled release properties. For intravenous administration the preferred carriers are for example physiological saline or phosphate buffered saline. An oligonucleotide and/or a pharmaceutical composition comprising such oligonucleotide for oral administration includes for example powder or granule, microparticulate, nanoparticulate, suspension or solution in water or non-aqueous media, capsule, gel capsule, sachet, tablet or minitablet. An oligonucleotide and/or a pharmaceutical composition comprising for parenteral, intrathecal, intracameral or intraventricular administration includes for example sterile aqueous solutions which optionally contain buffer, diluent and/or other suitable additive such as penetration enhancer, carrier compound and/or other pharmaceutically acceptable carrier or excipient.

A pharmaceutically acceptable carrier is for example liquid or solid, and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, a binding agent (e.g. pregelatinized maize starch, polyvinylpyrrolidone or hydroxypropyl methylcellulose, etc.); filler (e.g. lactose and other sugars, microcrystalline cellulose, pectin, gelatin, calcium sulfate, ethyl cellulose, polyacrylates or calcium hydrogen phosphate, etc.); lubricant (e.g., magnesium stearate, talcum, silica, colloidal silicon dioxide, stearic acid, metallic stearates, hydrogenated vegetable oils, corn starch, polyethylene glycols, sodium benzoate, sodium acetate, etc.); disintegrate (e.g., starch, sodium starch glycolate, etc.); or wetting agent (e.g., sodium lauryl sulfate, etc.). Sustained release oral delivery systems and/or enteric coatings for orally administered dosage forms are described in U.S. Pat. Nos. 4,704,295; 4,556,552; 4,309,406; and 4,309,404. An adjuvant is included under these phrases.

Besides being used in a method of human disease prevention and/or treatment, the oligonucleotide and/or the pharmaceutical composition according to the present invention is also used in a method for prevention and/or treatment of other subjects including veterinary animals, reptiles, birds, exotic animals and farm animals, including mammals, rodents, and the like. Mammals include for example horses, dogs, pigs, cats, or primates (for example, a monkey, a chimpanzee, or a lemur). Rodents include for example rats, rabbits, mice, squirrels, or guinea pigs.

In a third aspect, the present invention relates to the oligonucleotide of to the present invention or a pharmaceutical composition comprising the oligonucleotide of to the present invention for use in a method of preventing and/or treating a disease or disorder selected from the list of: an acute inflammatory disease, and a chronic inflammatory disease, a neurodegenerative disease, a malignant tumor, and a benign tumor.

In a fourth aspect, the present invention relates to a method of preventing and/or treating a disease or disorder selected from the list of: an acute inflammatory disease, a chronic inflammatory disease, a neurodegenerative disease, a malignant tumor, and a benign tumor, comprising the step of administering an oligonucleotide of to the present invention or the pharmaceutical composition of to the present invention to a patient in need thereof In particular embodiments of the present invention, the inflammatory disease is selected from the group consisting of: psoriasis, rheumatoid arthritis (RA), Morbus Bechterew, multiple sclerosis (MS), systemic lupus erythematosus (SLE), Behcet's disease, uveitis, Sjögren syndrome, an inflammatory bowel disease (IBD), asthma, chronic obstructive pulmonary disease (COPD), neuropathic pain, atopic dermatitis, and allergy.

In particular other embodiments of the present invention, the tumor is selected from the group consisting of solid tumors, blood born tumors, leukemias, tumor metastasis, hemangiomas, acoustic neuromas, neurofibromas, trachomas, pyogenic granulomas, psoriasis, astrocytoma, acoustic neuroma, blastoma, Ewing's tumor, craniopharyngioma, ependymoma, medulloblastoma, glioma, hemangioblastoma, Hodgkin's lymphoma, medullablastoma, leukaemia, mesothelioma, neuroblastoma, neurofibroma, non-Hodgkin's lymphoma, pinealoma, retinoblastoma, sarcoma, seminoma, trachomas, and Wilms' tumor, or is selected from the group of bile duct carcinoma, bladder carcinoma, brain tumor, breast cancer, bronchogenic carcinoma, carcinoma of the kidney, cervical cancer, choriocarcinoma, choroid carcinoma, cystadenocarcinoma, embryonal carcinoma, epithelial carcinoma, esophageal cancer, cervical carcinoma, colon carcinoma, colorectal carcinoma, endometrial cancer, gallbladder cancer, gastric cancer, head cancer, liver carcinoma, lung carcinoma, medullary carcinoma, neck cancer, non-small-cell bronchogenic/lung carcinoma, ovarian cancer, pancreas carcinoma, papillary carcinoma, papillary adenocarcinoma, prostate cancer, small intestine carcinoma, prostate carcinoma, rectal carcinoma, renal cell carcinoma, retinoblastoma, skin cancer, small-cell bronchogenic/lung carcinoma, squamous cell carcinoma, sebaceous gland carcinoma, testicular carcinoma, and uterine cancer.

For the purpose of clarity and a concise description, features are described herein as part of the same or separate embodiments, however, it will be appreciated that the scope of the invention may include embodiments having combinations of all or some of the features described.

The following examples will serve to further illustrate the present invention without, at the same time, however, constituting any limitation thereof. On the contrary, it is to be clearly understood that the scope of the present invention refers to various other embodiments, modifications, and equivalents thereof which, after reading the description herein, may suggest themselves to those skilled in the art without departing from the spirit of the invention.

EXAMPLES

Example 1: Sequence Selection and Oligonucleotide Modification Process

At first suitable sequences representing possible target sites were identified using proprietary bioinformatics tools. In a second step the effects of chemical modifications on these sequences were predicted in silico to optimize modification patterns.

1. Stepwise Sequence Selection Process.

For RORC two isoforms that arise from differential promoter usage and thus differ in their first exon are known. These two transcript variants are annotated as: NM_005060 for ROR gamma (RORC1) and NM_001001523 for ROR gamma t (RORC2). The variant RORC2 differs in the 5' UTR and coding region compared to variant RORC1. Therefore isoform RORC2 is shorter and has a distinct N-terminus compared to isoform RORC1. The mRNAs of RORC2 (NM_001001523) and RORC1 (NM_005060) consist of 3054 nucleotides and 3084 nucleotides, respectively. Alignment of both sequences shows that only the first 148 nucleotides mostly located within the 5'untranslated region (UTR) are unique to RORC2 while the remaining nucleotides are shared.

Sequence lengths ranging from 13 mer length to 17 mer length in this region were analyzed (800 sequences in total) using proprietary bioinformatic tools.

Following factors were considered for selection of RORC2-specific antisense sequences:

At least 3 mismatches to RORC1 mRNA
Low number of partially homologous potential off-target mRNAs
Cross-reactivity to mouse RORC2

2. Analysis of the Effects of Chemical Modifications

The effects of chemical modifications on physicochemical properties such as melting temperature and tendency to form hairpins or dimers were evaluated using available prediction tools. Oligonucleotides with the most favorable predicted physicochemical properties were selected for synthesis and screen.

Example 2: Inhibition of RORC2 with Antisense Oligonucleotides or DNAzymes

Material:
HDLM2 cell line—DSMZ (Deutsche Sammlung für Mikroorganismen and Zelllinien, Braunschweig, Germany/ACC-17)

TABLE 1

List of unmodified DNAzymes:

| Name | Position on NM_001001523 | DNAzyme Sequence 5'-3' | SEQ ID NO: |
|---|---|---|---|
| D01001HM | 145-163 | TCACTTCAAGGCTAGCTACAACGATTGTGTTCT | 76 |
| D01002HM | 137-153 | TTGTGTTCTCAGGCTAGCTACAACGAGACTG | 77 |
| D01003H | 130-148 | TTCTCATGAGGCTAGCTACAACGATGAGCCTTG | 78 |
| D01004H | 2-20 | AGCTCTGCAGGCTAGCTACAACGACTAGCTCTC | 79 |

TABLE 2

List of LNA - modified DNAzymes (+: LNA modification):

| Name | Position on NM_001001523 | DNAzyme Sequence 5'-3' | SEQ ID NO: |
|---|---|---|---|
| D01005HM | 145-163 | + T + C + ACTTCAAGGCTAGCTACAACGATTGTGT + T + C + T | 40 |
| D01006HM | 145-163 | + TCACTT + CAAGGCTAGCTACAACGATT + GTGTTC + T | 41 |
| D01007HM | 140-160 | + CTT + CAAGGCTAGCTACAACGATT + G + TGTTCTCAT + G + A | 42 |
| D01008HM | 142-160 | + CTT + CAAGGCTAGCTACAACGATT + GTGTTCTCA + T | 43 |
| D01009HM | 146-161 | + ACTT + CAAGGCTAGCTACAACGATTGT + GTT + C | 44 |
| D01010HM | 137-153 | + TTGTGTTCTCAGGCTAGCTACAACGAG + ACT + G | 45 |
| D01011H | 130-148 | + T + TCTCATGAGGCTAGCTACAACGATGAG + CCTT + G | 46 |
| D01012H | 131-145 | + TC + ATGAGGCTAGCTACAACGATGAG + CCT + T | 47 |
| D01013H | 2-20 | + AGCT + CTGCAGGCTAGCTACAACGACTAGCTC + T + C | 48 |
| D01014H | 2-19 | + GCTCTGCAGGCTAGCTACAACGACTAGCTCT + C | 49 |
| D01015H | 3-19 | + GCTCTGCAGGCTAGCTACAACGACTAGCTC + T | 50 |
| D01016H | 4-19 | + GCTCTGCAGGCTAGCTACAACGACTAGCT + C | 51 |
| D01017H | 4-19 | + GCTC + TGCAGGCTAGCTACAACGACT + AGCT + C | 52 |

TABLE 3

List of antisense oligonucleotides (+: LNA modification; *: PTO = phosphorothioate) and RORC2 knock-down effectiveness in HDLM2 cells:

| Name | Position on NM_001001523 | Antisense Sequence 5'-3' | Length | % residual RORC2 mRNA | SEQ ID NO: |
|---|---|---|---|---|---|
| A01018HM | 145-159 | + T* + T* + C*A*A*T*T*T*G*T*G*T* + T* + C + T | 15 | 5.20% | 2 |
| A01010HM | 138-154 | + T* + T* + T*G*T*G*T*T*C*T*C*A*T*G* + A* + C + T | 17 | 5.80% | 3 |
| A01011HM | 139-154 | + T* + T* + T*G*T*G*T*T*C*T*C*A*T* + G* + A* + C | 16 | 7.00% | 4 |
| A01017HM | 144-159 | + T* + T* + C*A*A*T*T*T*G*T*G*T*T*C* + T* + C | 16 | | 5 |
| A01019HM | 145-161 | + A* + C*T* + T*C*A*A*T*T*T*G*T*G*T* + T* + C* + T | 17 | 9.10% | 6 |
| A01021HM | 146-162 | + C* + A* + C*T*T*C*A*A*T*T*T*G*T*G* + T* + T* + C | 17 | 10.00% | 7 |
| A01016HM | 143-158 | + T* + C*A* + A*T*T*T*G*T*G*T*T*C* + T* + C* + A | 16 | 12.40% | 8 |
| A01007HM | 137-151 | + G* + T*G*T*T*C*T*C*A*T*G*A* + C*T* + G | 15 | 12.90% | 9 |
| A01012HM | 139-155 | + A* + T* + T*G*T*G*T*T*C*T*C*A*T* + G* + A* + C | 17 | 17.30% | 10 |
| A01015HM | 142-158 | + T* + C*A*A*T*T*T*G*T*G*T*T*C* + T* + C*A* + T | 17 | 19.40% | 11 |

TABLE 3-continued

List of antisense oligonucleotides (+: LNA modification; *: PTO = phosphorothioate) and RORC2 knock-down effectiveness in HDLM2 cells:

| Name | Position on NM_001001523 | Antisense Sequence 5'-3' | Length | % residual RORC2 mRNA | SEQ ID NO: |
|---|---|---|---|---|---|
| A01013HM | 140-155 | +A* +T* +T*T*G*T*G*T*T*C*T*C*A*T* +G* +A | 16 | 20.20% | 12 |
| A01003HM | 135-151 | +G*T* +G* +T*T*C*T*C*A*T*G*A*C*T*G* +A* +G | 17 | 26.30% | 13 |
| A01006HM | 136-151 | +G* +T* +G*T*T*C*T*C*A*T*G*A*C* +T* +G* +A | 16 | 24.60% | 14 |
| A01009HM | 138-153 | +T* +T*G* +T*G*T*T*C*T*C*A*T*G* +A* +C* +T | 16 | 24.60% | 15 |
| A01005HM | 136-152 | +T*G*T* +G* +T*T*C*T*C*A*T*G*A*C* +T* +G* +A | 17 | 29.10% | 16 |
| A01004HM | 136-151 | +G*T* +G*T*T*C*T*C*A*T*G*A*C* +T*G* +A | 16 | 23.50% | 17 |
| A01001HM | 103-118 | +C* +T*T*G*G*C*T*C*C*C*T*G*T* +C*C* +T | 16 | 33.00% | 18 |
| A01020HM | 146-161 | +A* +C*T* +T*C*A*A*T*T*T*G*T*G* +T* +T* +C | 16 | 34.00% | 19 |
| A01022HM | 147-163 | +T* +C*A*C* +T*T*C*A*A*T*T*T*G*T* +G* +T* +T | 17 | 37.90% | 20 |
| A01014HM | 141-157 | +C*A* +A* +T*T*T*G*T*G*T*T*C* +T*C* +A*T* +G | 17 | 35.90% | 21 |
| A01029H | 57-72 | +G*C* +A*G*C*T*G*G*C*G*G*C*A* +G* +A* +G | 16 | 42.00% | 22 |
| A01037HM | 143-159 | +T* +T* +C*A*A*T*T*T*G*T*G*T*T*C* +T* +C* +A | 17 | 12.00% | 23 |
| A01031HM | 135-151 | +G* +T* +G*T*T*C*T*C*A*T*G*A*C*T* +G* +A* +G | 17 | 17.00% | 24 |
| A01035HM | 136-151 | +G* +T*G*T*T*C*T*C*A*T*G*A*C* +T* +G* +A | 16 | 17.00% | 25 |
| A01036HM | 143-158 | +T* +C*A*A*T*T*T*G*T*G*T*T*C* +T* +C* +A | 16 | 20.00% | 26 |
| A01033HM | 136-151 | +G* +T* +G*T*T*C*T*C*A*T*G*A*C* +T* +G* +A | 16 | 23.00% | 27 |
| A01034HM | 136-151 | +G* +T* +G*T*T*C*T*C*A*T*G*A*C*T* +G* +A | 16 | | 28 |
| A01032HM | 135-151 | +G*T* +G*T*T*C*T*C*A*T*G*A*C*T* +G* +A* +G | 17 | | 29 |
| A01039HM | 145-161 | +A* +C* +T*T*C*A*A*T*T*T*G*T*G*T* +T* +C* +T | 17 | | 30 |
| A01024H | 6-22 | +G* +A* +A*G*C*T*C*T*G*C*A*C*C*T* +A*G* +C | 17 | 38.40% | 31 |
| A01023H | 4-19 | +G*C* +T*C*T*G*C*A*C*C*T*A*G*C* +T* +C | 16 | 41.00% | 32 |
| A01027H | 36-50 | +C*G* +A*G*G*C*C*C*T*C*T*C* +A* +G* +C | 15 | 45.30% | 33 |
| A01030HM | 103-118 | +C* +T*T*G*G*C*T*C*C*C*T*G*T*C* +C* +T | 16 | 46.00% | 34 |
| A01028H | 38-52 | +G*G* +C*G*A*G*G*C*C*C*T*C* +T* +C* +A | 15 | 53.80% | 35 |
| A01026H | 8-21 | +A* +A* +G*C*T*C*T*G*C*A*C* +C*T* +A | 14 | 57.20% | 36 |
| A01008HM | 138-152 | +T* +G* +T*G*T*T*C*T*C*A*T*G* +A* +C* +T | 15 | 60.90% | 37 |
| A01025H | 7-22 | +G* +A* +A*G*C*T*C*T*G*C*A*C*C* +T* +A* +G | 16 | 66.40% | 38 |
| A01002HM | 103-117 | +T* +T* +G*G*C*T*C*C*C*T*G*T* +C*C* +T | 15 | 79.80% | 39 |

Protocol:

HDLM2 cell line was purchased from DSMZ, expanded for master and working cell banks and cultured in supplemented RPMI 1640 medium (5% $CO_2$ and 37° C.) for all further experiments. The cultivation periods of every thawed cell batch from the working cell bank were between two and three weeks.

All oligonucleotides were ordered from Exiqon (Vedbaek/Denmark) and Biospring (Frankfurt/Germany). The lyophilized oligonucleotides were reconstituted with DEPC treated water to concentration of 1 mM.

The initial screen was performed in HDLM2 cell line at single concentration of 10 μM for each RORC2-specific oligonucleotide and negative control (neg1; described in WO2014154843A1). Cells were treated with oligonucleotides without any transfection reagent (gymnotic delivery) and lysed after three days to determine knock-down of RORC2.

Results:

The initial screen of antisense oligonucleotides in HDLM2 cells resulted in several highly active molecules. RORC2 and HPRT1 mRNA levels were determined by Quantigene Singleplex bDNA assay. RORC2 mRNA levels were normalized to HPRT1 levels (housekeeping gene) and related to untreated control (FIG. 2A). Mean values of RORC2 mRNA expression after normalization are listed for each oligonucleotide in Tab. 3. The best knock-down efficiency was achieved with two oligonucleotides—A01018HM (94.8%) and A01010HM (94.2%).

Figure 2B:
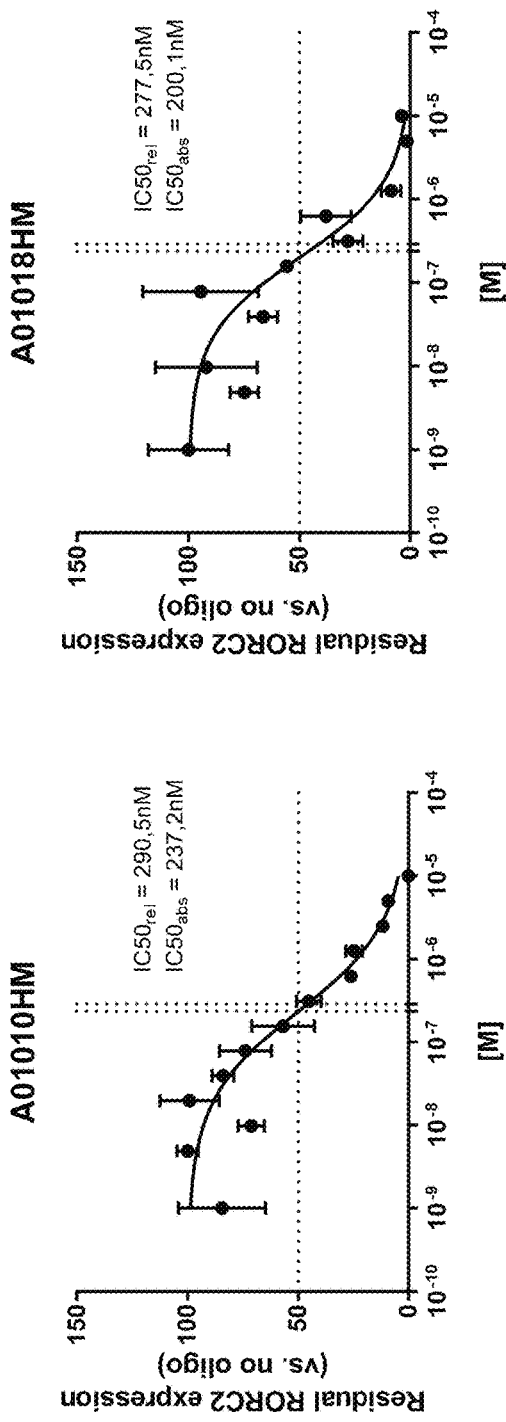
FIG. 2B shows $IC_{50}$ determination for two RORC2 specific oligonucleotides. The plots show decreasing residual RORC2 mRNA expression (y axes) in dependence of ASO concentration (x axes).

For further characterization of these two oligonucleotides, we performed a dose-response experiment. We treated HDLM2 cells with serially diluted oligonucleotides for three days and determined the residual RORC2 mRNA via Quantigene Singleplex bDNA Assay (FIG. 2B). The IC50 values for A01010HM are 290.5 nM (relative) and 237.2 nM (absolute; with knock-down of 99.7% at highest concentration of 10 μM). For A01018HM relative $IC_{50}$ is 277.5 nM and absolute 200.1 nM (maximal knock-down of 96.2%).

Dose-Dependent Knock-Down of RORC2 Protein

Figure 2C:
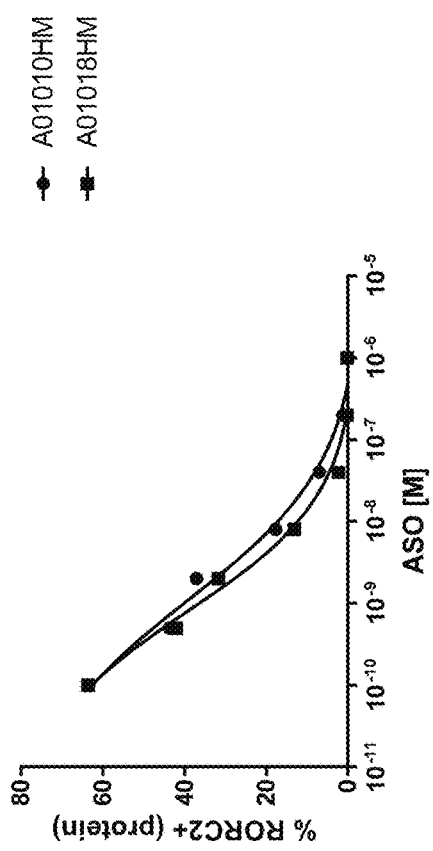
FIG. 2C shows RORC2 protein expression (y axes) in presence of titrated amounts of two examples of RORC2 specific oligonucleotides (x axes).

In order to determine knock-down efficacy on the protein level, we transfected human cancer cell line, Hela with a plasmid construct coding for N-terminally, his-tagged RORC2 protein and treated them with titrated amounts of respective oligonucleotide. The knock-down efficacy was determined by FACS co-staining of RORC2 and his tag (FIG. 2C).

Effects on RORC Isoform 1 and 2

Figure 2D:
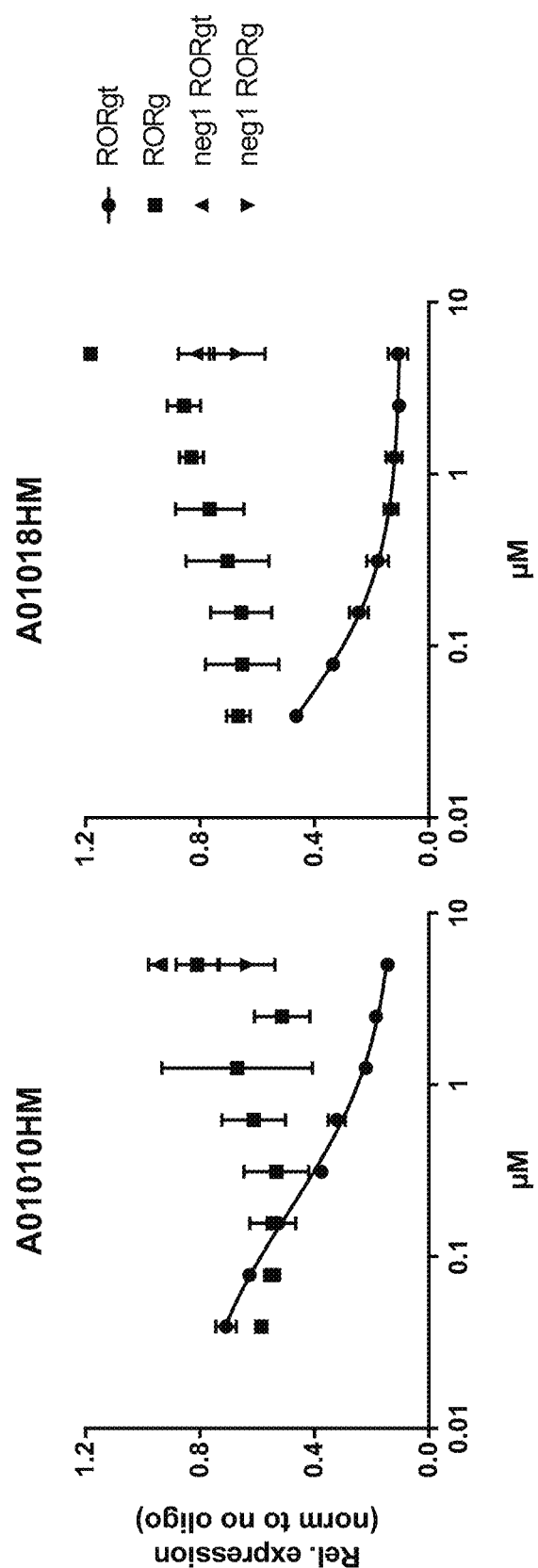
FIG. 2D shows effects on both RORC isoforms, RORC1 and RORC2 in presence of RORC2 specific and control ASOs.

Two of RORC isoforms differ in their 5' regions, expression patterns and biological functions. In order to interfere with Th17- and therefore RORC2-driven autoimmune phenotypes we aim to specifically target RORC2. We analyzed the ASO effects on both RORC1 and RORC2 mRNA in HDLM2 cells upon three days of treatment and observed mostly unaffected RORC1 mRNA expression while RORC2 was dose-dependently knocked down (FIG. 2D).

ASO Effects in Primary Human Th17 Cells

The next step of knock-down efficacy was performed in polarized human Th17 cells. Th17 cells were generated from human donors' blood according to Acosta-Rodriguez et al. (Nat Immunol 2007). During the polarization process human T cells were treated with oligonucleotides. The primary readout was the RORC2 knock-down followed by its downstream effects IL17A/F, IL22 cytokine production.

Figure 2E:
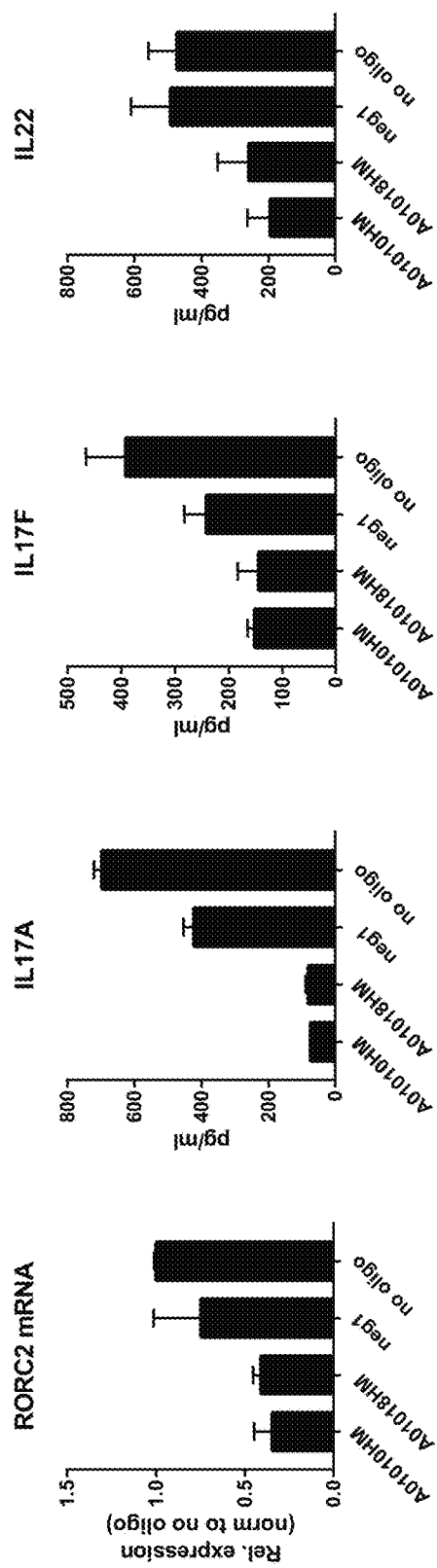
FIG. 2E shows knock-down efficacy of two specific oligonucleotides in human Th17 cells and reduction of major Th17-characteristic cytokines, IL17A/F and IL22.
Figure 2F:
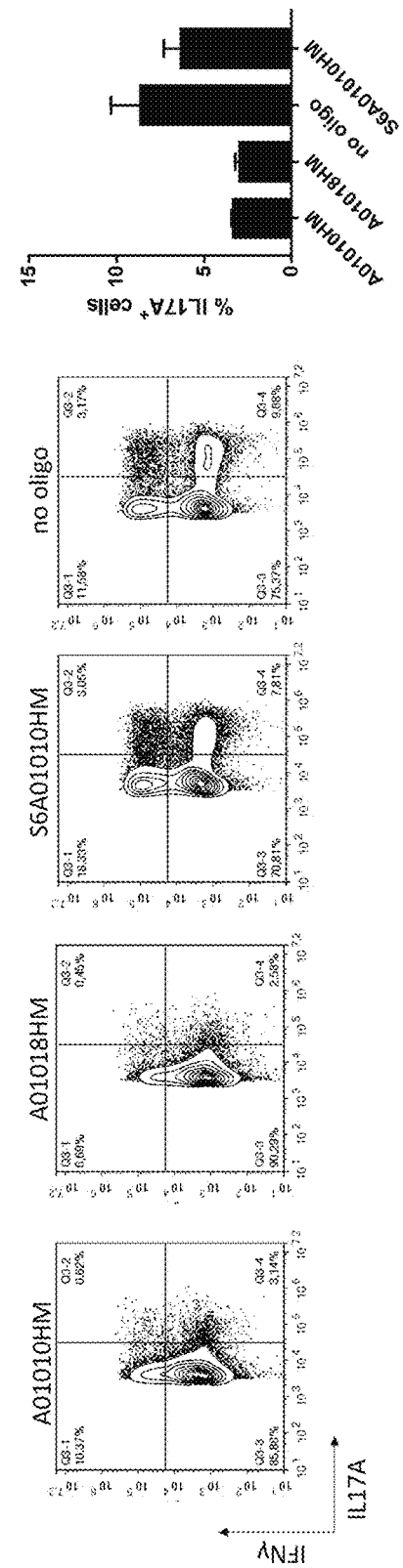
FIG. 2F shows IL17A production in human Th17 cells via florescence associated cell sorting (FACS).

The presence of ASOs during the polarization reduced the expression of RORC2 mRNA by at least 50%. Further, reduction of IL17A/F and IL22 cytokine secretion was observed in RORC2-specific ASO treated groups (FIG. 2E/F).

RORC2-Specific ASOs in TNBS-Induced Colitis Mouse Model

Figure 2G:
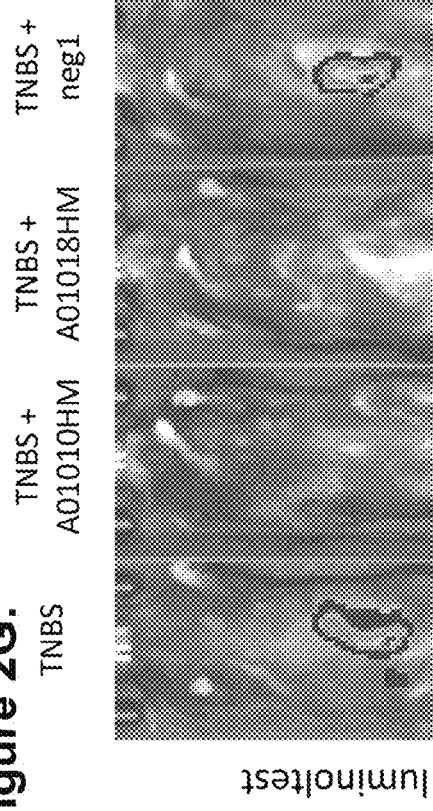
FIG. 2G shows luminol test results in TNBS-induced colitis model for two RORC2 specific oligonucleotides and neg1 control.
Figure 2H:
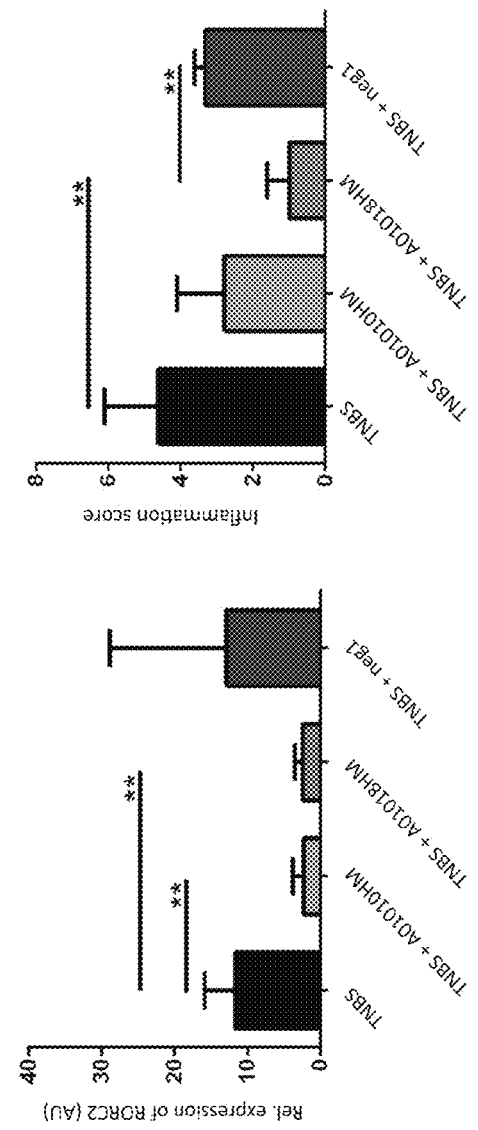
FIG. 2H shows reduction in RORC2 expression and inflammation score of mice colons in TNBS model.
Figure 2I:
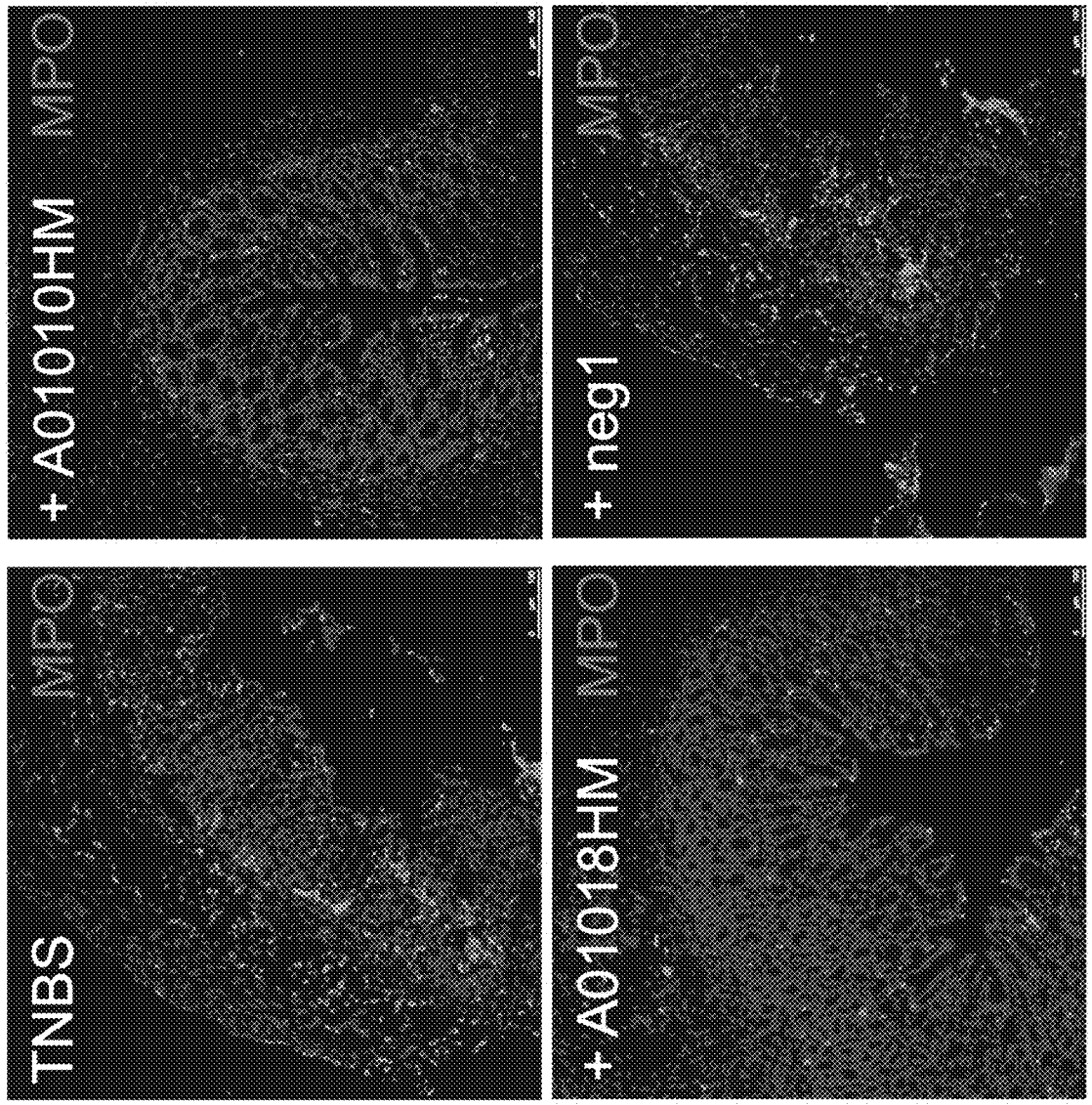
FIG. 2I shows myeloperoxidase expression in mice colons of each experimental group (red dots—myeloperoxidase; blue staining—DAPI).

In order to validate the effects of RORC2 knock-down in a Th17 relevant disease model, we treated mice with 1 mg/kg (i.r.) of RORC2-specific ASOs (A01010HM, A01018HM) or negative control (neg1). Mice were treated two times prior and two times during colitis-inducing challenge and disease exacerbation. At the end-point of ten-day experiment, we measured RORC2 knock-down, inflammation score and myeloperoxidase expression in colon. Both A01010HM and A01018HM reduce expression of RORC2 in colon and overall inflammation (luminol test) (FIG. 2G/H). The inflammation score represents overall changes in mucocutaneous gut parameters and is reduced in presence of RORC2-specific ASOs (FIG. 2H). Further, the expression of proinflammatory myeloperoxidase throughout the colon is reduced with RORC2 knock-down (FIG. 2I). Taken together, presented ASOs have potent knock-down efficacy in vivo and counteract inflammation in TNBS-induced colitis model.

Example 3: Hit-to-Lead Optimization of RORC2-Specific Antisense Oligonucleotides Initially identified antisense oligonucleotides with the highest knock-down efficacy bind in the unique exon-exon junction site generated exclusively in RORC2 spliced mRNA sequence. Newly designed and screened ASOs bind to the unique RORC2 sequence too. This unique RORC2 sequence is (5'-3', mRNA):

AAGGCTCAGTCATGAGAACACAAATTGAAGTGATCC (SEQ ID NO: 80)

Figure 4:
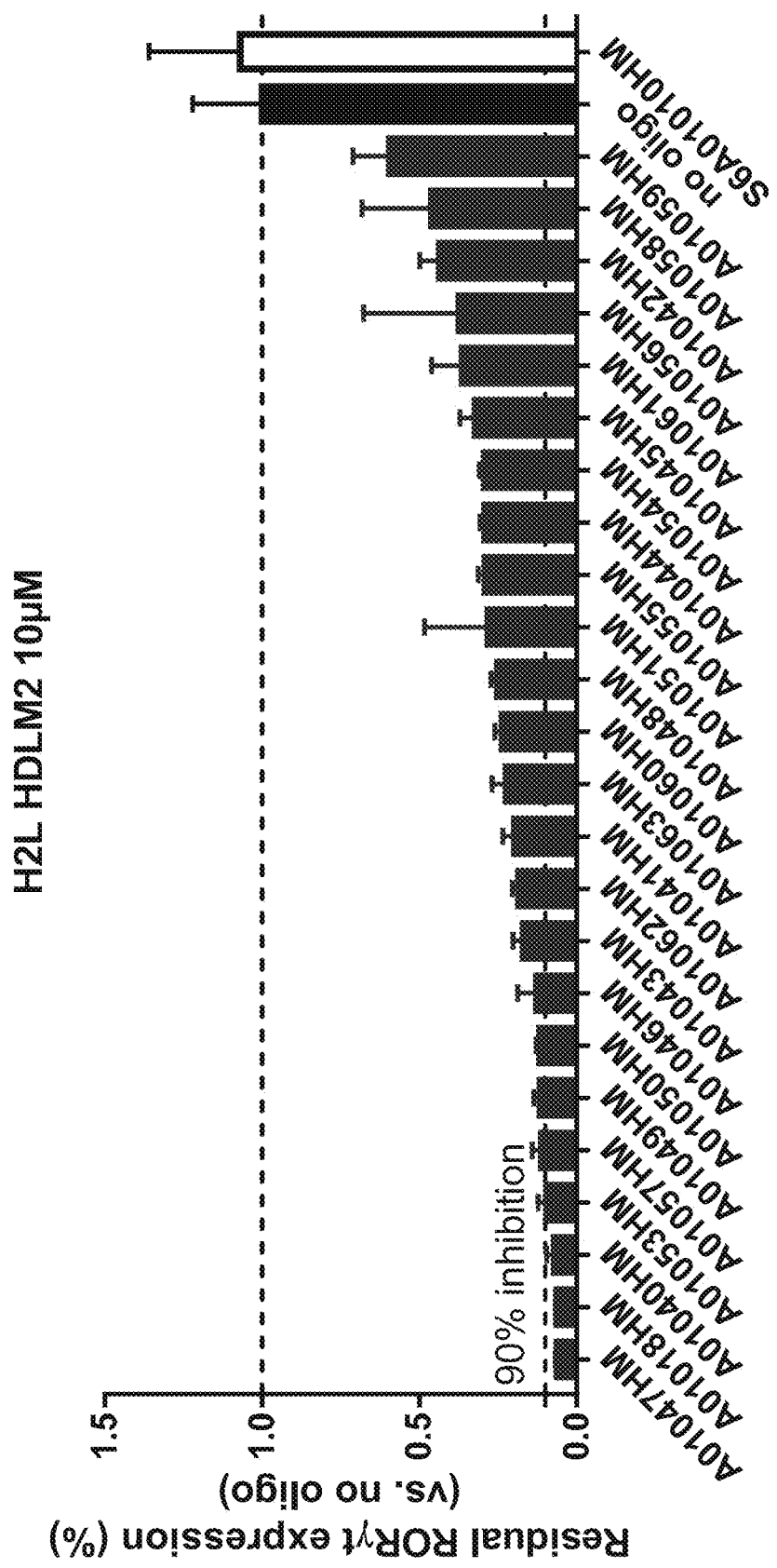
FIG. 4 shows the result of a further oligonucleotide screen for RORC2 inhibition in HDLM2 cells, as described in Example 3.

The single-dose screen of antisense oligonucleotides in HDLM2 cells resulted in several highly active molecules. RORC2 and HPRT1 mRNA levels were determined by bDNA assay. RORC2 mRNA levels were normalized to HPRT1 levels (housekeeping gene) and related to untreated control (FIG. 4). Mean values of RORC2 mRNA expression after normalization are listed for each oligonucleotide in Tab. 4. A01018HM (the most efficient antisense oligonucleotide from the initial screens) was used as internal control.

TABLE 4

List of antisense oligonucleotides (+: LNA modification; *: PTO = phosphorothioate) and RORC2 knock-down effectiveness in HDLM2 cells [X: undisclosed nucleotide]

| Name | Position on NM_001001523 | Antisense Sequence 5'-3' | Length | % residual RORC2 mRNA | SEQ ID NO: |
|---|---|---|---|---|---|
| A01047HM | 136-154 | + T* + T* + T*G*T*G*T*T*C*T*C*A*T*G*A*C* + T* + G* + A | 19 | 6.26% | 53 |
| A01018HM | 145-159 | + T* + T* + C*A*A*T*T*T*G*T*G*T* + T* + C* + T | 15 | 6.40% | 2 |
| A01040HM | 136-153 | + T* + T* + G*T*G*T*T*C*T*C*A*T*G*A*C* + T* + G* + A | 18 | 7.10% | 54 |
| A01053HM | 136-155 | + A* + T* + T*T*G*T*G*T*T*C*T*C*A*T*G*A*C* + T* + G* + A | 20 | 9.67% | 55 |
| A01057HM | 144-163 | + T* + C* + A*C*T*T*C*A*A*T*T*T*G*T*G*T*T* + C* + T* + C | 20 | 11.32% | 56 |
| A01049HM | 144-162 | + C* + A* + C*T*T*C*A*A*T*T*T*G*T*G*T*T* + C* + T* + C | 19 | 11.63% | 57 |
| A01050HM | 145-163 | + T* + C* + A*C*T*T*C*A*A*T*T*T*G*T*G*T* + T* + C* + T | 19 | 11.86% | 58 |
| A01046HM | 146-63 | + T* + C* + A*C*T*T*C*A*A*T*T*T*G*T*G* + T* + T* + C | 18 | 12.83% | 59 |
| A01043HM | 142-159 | + T* + T* + C*A*A*T*T*T*G*T*G*T*T*C*T* + C* + A* + T | 18 | 17.02% | 60 |

TABLE 4-continued

List of antisense oligonucleotides (+: LNA modification; *: PTO = phosphorothioate) and RORC2 knock-down effectiveness in HDLM2 cells [X: undisclosed nucleotide]

| Name | Position on NM_001001523 | Antisense Sequence 5'-3' | Length | % residual RORC2 mRNA | SEQ ID NO: |
|---|---|---|---|---|---|
| A01062HM | 143-163 | +T* +C* +A*C*T*T*C*A*A*T*T*T*G*T*G*T*T*C* +T* +C* +A | 21 | 18.58% | 61 |
| A01041HM | 138-155 | +A* +T* +T*T*G*T*G*T*T*C*T*C*A*T*G* +A* +C* +T | 18 | 19.75% | 62 |
| A01063HM | ex 131 to 166 | +X* +X* +X*X*X*X*X*X*X*X*X*X*X*X*X*X* +X* +X* +X | 18 to 21 | 22.51% | 63 |
| A01060HM | ex 131 to 166 | +X* +X* +X*X*X*X*X*X*X*X*X*X*X*X*X*X* +X* +X* +X | 18 to 21 | 23.71% | 64 |
| A01048HM | ex 131 to 166 | +X* +X* +X*X*X*X*X*X*X*X*X*X*X*X*X* +X* +X* +X | 18 to 21 | 25.24% | 65 |
| A01051HM | ex 131 to 166 | +X* +X* +X*X*X*X*X*X*X*X*X*X*X*X*X* +X* +X | 18 to 21 | 28.17% | 66 |
| A01051HM | ex 131 to 166 | +X* +X* +X*X*X*X*X*X*X*X*X*X*X*X*X* +X* +X | 18 to 21 | 28.17% | 66 |
| A01055HM | ex 131 to 166 | +X* +X* +X*X*X*X*X*X*X*X*X*X*X*X*X*X* +X* +X* +X | 18 to 21 | 29.21% | 67 |
| A01044HM | ex 131 to 166 | +X* +X* +X*X*X*X*X*X*X*X*X*X*X*X* +X* +X* +X | 18 to 21 | 29.31% | 68 |
| A01054HM | ex 131 to 166 | +X* +X* +X*X*X*X*X*X*X*X*X*X*X*X*X*X* +X* +X* +X | 18 to 21 | 29.44% | 69 |
| A01045HM | ex 131 to 166 | +X* +X* +X*X*X*X*X*X*X*X*X*X*X*X*X* +X* +X* +X | 18 to 21 | 32.49% | 70 |
| A01061HM | ex 131 to 166 | +X* +X* +X*X*X*X*X*X*X*X*X*X*X*X*X*X*X* +X* +X* +X | 18 to 21 | 36.40% | 71 |
| A01056HM | ex 131 to 166 | +X* +X* +X*X*X*X*X*X*X*X*X*X*X*X*X*X* +X* +X* +X | 18 to 21 | 37.38% | 72 |
| A01042HM | ex 131 to 166 | +X* +X* +X*X*X*X*X*X*X*X*X*X*X*X* +X* +X* +X | 18 to 21 | 43.80% | 73 |
| A01058HM | ex 131 to 166 | +X* +X* +X*X*X*X*X*X*X*X*X*X*X*X*X*X* +X* +X* +X | 18 to 21 | 46.15% | 74 |
| A01059HM | ex 131 to 166 | +X* +X* +X*X*X*X*X*X*X*X*X*X*X*X*X*X* +X* +X* +X | 18 to 21 | 59.62% | 75 |

TABLE 5

Sequence ID Nos:

| SEQ ID No: | Sequence identifier |
|---|---|
| 1 | RORC2 sequence (see FIG. 1) |
| 2 | A01018HM |
| 3 | A01010HM |
| 4 | A01011HM |
| 5 | A01017HM |
| 6 | A01019HM |
| 7 | A01021HM |
| 8 | A01016HM |
| 9 | A01007HM |
| 10 | A01012HM |
| 11 | A01015HM |
| 12 | A01013HM |
| 13 | A01003HM |
| 14 | A01006HM |
| 15 | A01009HM |
| 16 | A01005HM |
| 17 | A01004HM |
| 18 | A01001HM |
| 19 | A01020HM |
| 20 | A01022HM |
| 21 | A01014HM |
| 22 | A01029H |
| 23 | A01037HM |
| 24 | A01031HM |
| 25 | A01035HM |
| 26 | A01036HM |
| 27 | A01033HM |
| 28 | A01034HM |
| 29 | A01032HM |
| 30 | A01039HM |
| 31 | A01024H |
| 32 | A01023H |
| 33 | A01027H |
| 34 | A01030HM |
| 35 | A01028H |
| 36 | A01026H |
| 37 | A01008HM |
| 38 | A01025H |
| 39 | A01002HM |
| 40 | D01005HM |
| 41 | D01006HM |
| 42 | D01007HM |
| 43 | D01008HM |
| 44 | D01009HM |
| 45 | D01010HM |
| 46 | D01011H |
| 47 | D01012H |
| 48 | D01013H |
| 49 | D01014H |
| 50 | D01015H |
| 51 | D01016H |
| 52 | D01017H |
| 53 | A01047HM |
| 54 | A01040HM |
| 55 | A01053HM |
| 56 | A01057HM |

TABLE 5-continued

| SEQ ID No: | Sequence identifier |
|---|---|
| 57 | A01049HM |
| 58 | A01050HM |
| 59 | A01046HM |
| 60 | A01043HM |
| 61 | A01062HM |
| 62 | A01041HM |
| 63 | A01063HM |
| 64 | A01060HM |
| 65 | A01048HM |
| 66 | A01051HM |
| 67 | A01055HM |
| 68 | A01044HM |
| 69 | A01054HM |
| 70 | A01045HM |
| 71 | A01061HM |
| 72 | A01056HM |
| 73 | A01042HM |
| 74 | A01058HM |
| 75 | A01059HM |

The invention claimed is:

1. An oligonucleotide consisting of from 15 to 21 nucleotides, comprising the nucleic acid sequence of SEQ ID NO. 2, SEQ ID NO. 3, SEQ ID NO. 4, SEQ ID NO. 6, SEQ ID NO. 7, SEQ ID NO. 8, SEQ ID. NO. 9, SEQ ID NO. 10, SEQ ID NO. 11, SEQ ID NO. 23, SEQ ID NO. 24, SEQ ID NO. 25, SEQ ID NO. 26, SEQ ID NO. 53, SEQ ID NO. 54, SEQ ID NO. 55, SEQ ID NO. 56, SEQ ID NO. 57, SEQ ID NO. 58, SEQ ID NO. 59, SEQ ID NO. 60, SEQ ID NO. 61, or SEQ ID NO. 62, wherein the oligonucleotide is modified.

2. The oligonucleotide of claim 1, wherein said oligonucleotide inhibits the expression of retinoic acid receptor-related orphan receptor 2 (RORC2) relative to the expression of hypoxanthine-guanine phosphoribosyltransferase 1 (HPRT1) in Hodgkin lymphoma 2 (HDLM2) cells by at least 80%.

3. The oligonucleotide of claim 1, wherein one or more linkages between the nucleotides are phosphorothioates.

4. A pharmaceutical composition comprising the oligonucleotide according to claim 1 and a pharmaceutically acceptable carrier.

5. A method of treating a disease or disorder wherein the disease or disorder is an acute inflammatory disease, a chronic inflammatory disease, a neurodegenerative disease, a malignant tumor, or a benign tumor, comprising the step of administering an oligonucleotide according to claim 1 to a patient in need thereof.

6. The method of claim 5, wherein the inflammatory disease is psoriasis, rheumatoid arthritis (RA), Morbus Bechterew, multiple sclerosis (MS), systemic lupus erythematosus (SLE), Behcet's disease, uveitis, Sjögren syndrome, an inflammatory bowel disease (IBD), asthma, chronic obstructive pulmonary disease (COPD), neuropathic pain, atopic dermatitis, or allergy.

7. The method of claim 5, wherein the tumor is a solid tumor, a blood born tumor, a leukemia, a tumor metastasis, a hemangioma, an acoustic neuroma, a neurofibroma, a trachoma, a pyogenic granuloma, psoriasis, astrocytoma, acoustic neuroma, blastoma, Ewing's tumor, craniopharyngioma, ependymoma, medulloblastoma, glioma, hemangioblastoma, Hodgkin's lymphoma, medullablastoma, mesothelioma, neuroblastoma, neurofibroma, non-Hodgkin's lymphoma, pinealoma, retinoblastoma, sarcoma, seminoma, a trachoma, or Wilms' tumor.

8. The oligonucleotide of claim 1, consisting of from 15 to 20 nucleotides.

9. The oligonucleotide of claim 1, wherein said oligonucleotide inhibits the expression of retinoic acid receptor-related orphan receptor 2 (RORC2) relative to the expression of hypoxanthine-guanine phosphoribosyltransferase 1 (HPRT1) in Hodgkin lymphoma 2 (HDLM2) cells by at least 85%.

10. The oligonucleotide of claim 1, wherein said oligonucleotide inhibits the expression of retinoic acid receptor-related orphan receptor 2 (RORC2) relative to the expression of hypoxanthine-guanine phosphoribosyltransferase 1 (HPRT1) in Hodgkin lymphoma 2 (HDLM2) cells by at least 90%.

11. The oligonucleotide of claim 3, wherein all linkages are phosphorothioates.

12. The method of claim 5, wherein the tumor is a bile duct carcinoma, a bladder carcinoma, a brain tumor, breast cancer, a bronchogenic carcinoma, a carcinoma of the kidney, cervical cancer, a choriocarcinoma, a choroid carcinoma, a cystadenocarcinoma, an embryonal carcinoma, an epithelial carcinoma, esophageal cancer, a cervical carcinoma, a colon carcinoma, a colorectal carcinoma, endometrial cancer, gallbladder cancer, gastric cancer, head cancer, a liver carcinoma, a lung carcinoma, a medullary carcinoma, neck cancer, a non-small-cell bronchogenic/lung carcinoma, ovarian cancer, a pancreas carcinoma, a papillary carcinoma, a papillary adenocarcinoma, prostate cancer, a small intestine carcinoma, a prostate carcinoma, rectal cancer, a renal cell carcinoma, retinoblastoma, skin cancer, a small-cell bronchogenic/lung carcinoma, a squamous cell carcinoma, a sebaceous gland carcinoma, a testicular carcinoma, or uterine cancer.

* * * * *